US008791095B2

(12) United States Patent
Casebier

(10) Patent No.: US 8,791,095 B2
(45) Date of Patent: Jul. 29, 2014

(54) STEROIDAL CYP17 INHIBITORS/ANTIANDROGENS

(75) Inventor: David Casebier, Carlisle, MA (US)

(73) Assignee: Tokai Pharmaceuticals, Inc., Cambridge, MA (US)

(*) Notice: Subject to any disclaimer, the term of this patent is extended or adjusted under 35 U.S.C. 154(b) by 328 days.

(21) Appl. No.: 13/145,997

(22) PCT Filed: Feb. 5, 2010

(86) PCT No.: PCT/US2010/023387
§ 371 (c)(1),
(2), (4) Date: Sep. 6, 2011

(87) PCT Pub. No.: WO2010/091303
PCT Pub. Date: Aug. 12, 2010

(65) Prior Publication Data
US 2011/0312924 A1 Dec. 22, 2011

Related U.S. Application Data

(60) Provisional application No. 61/150,027, filed on Feb. 5, 2009.

(51) Int. Cl.
A61K 31/58 (2006.01)
C07J 43/00 (2006.01)

(52) U.S. Cl.
USPC ................... 514/176; 540/95; 540/96

(58) Field of Classification Search
USPC ..................... 540/95, 96; 514/176
See application file for complete search history.

(56) References Cited

U.S. PATENT DOCUMENTS

| 4,000,125 | A | 12/1976 | Casagrande et al. |
| 5,601,981 | A | 2/1997 | Malins |
| 5,604,213 | A | 2/1997 | Barrie et al. |
| 5,994,335 | A | 11/1999 | Brodie et al. |
| 6,200,965 | B1 | 3/2001 | Brodie et al. |
| 6,444,683 | B2 | 9/2002 | Brodie et al. |
| 7,875,599 | B2 | 1/2011 | Brodie |
| 2001/0001099 | A1 | 5/2001 | Brodie et al. |
| 2003/0054053 | A1 | 3/2003 | Young et al. |
| 2010/0047338 | A1 | 2/2010 | Brodie et al. |
| 2010/0048524 | A1 | 2/2010 | Brodie et al. |
| 2010/0048912 | A1 | 2/2010 | Brodie et al. |
| 2010/0048913 | A1 | 2/2010 | Brodie et al. |
| 2010/0048914 | A1 | 2/2010 | Brodie et al. |
| 2010/0137269 | A1 | 6/2010 | Brodie et al. |

FOREIGN PATENT DOCUMENTS

| GB | 2479337 | 10/2011 |
| WO | WO 2005/014023 A1 | 2/2005 |
| WO | WO 2006/093993 A1 | 9/2006 |
| WO | WO 2009/120565 A2 | 10/2009 |
| WO | WO 2009/120565 A3 | 3/2010 |

OTHER PUBLICATIONS

Clement, et al. Three dimensional pharmacophore modeling of human CYP17 inhibitors. Potential agents for prostate cancer therapy. J Med Chem. Jun. 5, 2003;46(12):2345-51.
Handratta, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. J Med Chem. Apr. 21, 2005;48(8):2972-84.
International search report dated Jul. 5, 2010 for PCT/US2010/023387.
Moreira, et al. Synthesis and evaluation of novel 17-indazole androstene derivatives designed as CYP17 inhibitors. Steroids. Dec. 2007;72(14):939-48.
Office Action dated Oct. 5, 2011 for U.S. Appl. No. 12/577,094.
Abstract ANIH Grant Project Reference No. 5RO1 CA27440-24, approximate date Feb. 20, 2003; approximate award date Jun. 3, 2003.
Abstract of NIH Grant Project Reference No. 2R01 CA27440-25A1, approximate submission date Feb. 18, 2004; approximate award date Sep. 23, 2004.
Abstract of NIH Grant Project Reference No. 3RO1 CA27440-22S1, approximate date Jun. 21, 2001; approximate award date Aug. 17, 2001.
Abstract of NIH Grant Project Reference No. 3RO1 CA27440-23S1, approximate date May 3, 2002; approximate award date Jun. 21, 2002.
Abstract of NIH Grant Project Reference No. 5RO1 CA27440-23, approximate date Jan. 21, 2002; approximate award date Apr. 29, 2002.
Abstract of NIH Grant Project Reference No. 5RO1 CA27440-24S1, approximate date Apr. 1, 2003; approximate award date Jun. 3, 2003.
Abstract of NIH Grant Project Reference No. 5RO1 CA27440-26, approximate submission date Jul. 1, 2005; approximate award date Aug. 2, 2005.
Abstract of NIH Grant Project Reference No. 5RO1CA27440-27, approximate submission date Apr. 26, 2006.

(Continued)

Primary Examiner — Barbara P Badio
(74) Attorney, Agent, or Firm — Wilson Sonsini Goodrich & Rosati

(57) ABSTRACT

Steroidal C-17 nitrogen-containing heterocycles of Formula I:

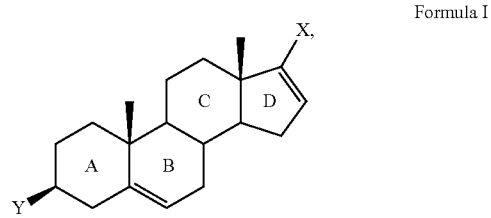

Formula I wherein: the ABCD ring structure is the nucleus of a steroid, or an analog thereof, X is a group capable of coordinating a heme group of CYP17, and Y is an hydroxyl functionality, a suitable ester, or a prodrug group, for the treatment of urogenital and/or androgen-related cancers, such as castration-resistant prostate cancer. The invention provides methods of synthesizing new chemical entities and methods of using the same in treating urogenital and/or androgen-related cancers.

27 Claims, No Drawings

(56) References Cited

OTHER PUBLICATIONS

Barrie, et al. Pharmacology of novel steroidal inhibitors of cytochrome P450(17) alpha (17 alpha-hydroxylase/C17-20 lyase). J Steroid Biochem Mol Biol. Sep. 1994;50(5-6):267-73.
Bruchovsky, et al. The conversion of testosterone to 5-alpha-androstan-17-beta-ol-3-one by rat prostate in vivo and in vitro. J Biol Chem. Apr. 25, 1968;243(8):2012-21.
Chen, et al. Molecular determinants of resistance to antiandrogen therapy. Nat Med. Jan. 2004;10(1):33-9.
Chengjie, et al. Synthesis of pharmacological activity of some 17-[(2'-substituted)-4'-pyramidyl] androstene derivatives as inhibitors of human 17alpha-hydroxylase/C17,20-layse. J. Chinese Pharm. Sci. 2001; 10(1):3-8.
Choshi, et al. Total synthesis of grossularines-1 and -2. J. Org. Chem. 1995; 60:5899-5904.
Crawford, et al. A controlled trial of leuprolide with and without flutamide in prostatic carcinoma. New Eng J Med. 1989; 321:419-424.
Crawford, et al. Treatment of newly diagnosed stage D2 prostate cancer with leuprolide and flutamide or leuprolide alone, phase III: prognostic significance of minimal disease. J. Urol. 1992; 147:417A.
Denis. Role of maximal androgen bloackade in advanced prostate cancer. The Prostate Supplement. 1994; 5:17-22.
Denmeade, et al. A history of prostate cancer treatment. Nat Rev Cancer. 2002; 2(5):389-96.
Evans, et al. methods for drug discovery: development of potent, selective, orally effective cholecystokinin antagonists. J Med Chem 1988; 31(12):2235-46.
Grigoryev, et al. Cytochrome P450c17-expressing *Escherichia coli* as a first-step screening system for 17alpha-hydroxylase-C17,20-lyase inhibitors. Anal Biochem. Feb. 15, 1999;267(2):319-30.
Grigoryev, et al. Effects of new 17alpha-hydroxylase/C(17,20)-lyase inhibitors on LNCaP prostate cancer cell growth in vitro and in vivo. Br J Cancer. Oct. 1999;81(4):622-30.
Haidar, et al. Effects of novel 17alpha-hydroxylase/C17, 20-lyase (P450 17, CYP 17) inhibitors on androgen biosynthesis in vitro and in vivo. J Steroid Biochem Mol Biol. Apr. 2003;84(5):555-62.
Haidar, et al. Novel steroidal pyrimidyl inhibitors of P450 17 (17 alpha-hydroxylase/C17-20-lyase). Arch Pharm (Weinheim). Dec. 2001;334(12):373-4.
Hall. Cytochrome P-450 C21scc: one enzyme with two actions: hydroxylase and lyase. J Steroid Biochem Mol Biol. 1991;40(4-6):527-32.
Handratta, et al, Potent CYP17 inhibitors: improved syntheses, pharmacokinetics and anti-tumor activity in the LNCaP human prostate cancer model. J Steroid Biochem Mol Biol. Oct. 2004;92(3):155-65.
Hartmann, et al. Synthesis and evaluation of novel steroidal oxime inhibitors of P450 17 (17 alpha-hydroxylase/C17-20-lyase) and 5 alpha-reductase types 1 and 2. J. Med. Chem. Nov. 2, 2000;43(22):4266-77.
Huggins, et al. Studies in prostate cancer: The effects of castration on advanced carcinoma of the prostate gland. Arch Surg. 1941; 43(2):209-223.
Humber; et al. Synthesis and biological activity of some cardiotonic compounds related to digitoxigenin. Steroids. Aug. 1983;42(2):189-202.
International search report dated Oct. 7, 2009 for PCT/US2009/036891.
Jarman, et al. The 16,17-double bond is needed for irreversible inhibition of human cytochrome p45017alpha by abiraterone (17-(3-pyridyl)androsta-5, 16-dien-3beta-ol) and related steroidal inhibitors. J Med Chem; Dec. 31, 1998;41(27):5375-81.
Jefcoate. Measurement of substrate and inhibitor binding to microsomal cytochrome P-450 by optical-difference spectroscopy. Methods Enzymol. 1978;52:258-79.
Jemal, et al. Cancer statistics, 2004. CA cancer J. Clin. 2004; 54(1):8-29.

Kadar, et al. Technical and safety aspects of blood and marrow transplantation using G-CSF mobilized family donors. Transfus Sci. Dec. 1996;17(4):611-8.
Kim, et al. Synergism of cytoplasmic kinases in IL6-induced ligand-independent activation of androgen receptor in prostate cancer cells. Oncogene. Mar. 11, 2004;23(10):1838-44.
Klein, et al. Progression of metastatic human prostate cancer to androgen independence in immunodeficient SCID mice. Nat Med. Apr. 1997;3(4):402-8.
Ling, et al. 17-Imidazolyl, pyrazolyl, and isoxazolyl androstene derivatives. Novel steroidal inhibitors of human cytochrome C17,20-lyase (P450(17 alpha). J Med Chem. Sep. 26, 1997;40(20):3297-304.
Long, et al. Antiandrogenic effects of novel androgen synthesis inhibitors on hormone-dependent prostate cancer. Cancer Res. Dec. 1, 2000;60(23):6630-40.
Matsunaga, et al. C17,20-lyase inhibitors I. Structure-based de novo design and SAR study of C17,20-lyase inhibitors. Bioorg Med Chem. May 1, 2004;12(9):2251-73.
Matsunaga, et al. Synthetic studies on (1S)-1-(6,7-dimethoxy-2-naphthyl)-1-(1H-imidazol-4-yl)-2-methylpropan-1-ol as a selective C17,20-lyase inhibitor. Tetrahedron: Asymmetry. 2004; 15:2021-2028.
Matsunaga, et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. Aug. 15, 2004;12(16):4313-36.
McConnell. Physiologic basis of endocrine therapy for prostatic cancer. Urol Clin North Am. Feb. 1991;18(1):1-13.
Mohler, et al. The androgen axis in recurrent prostate cancer. Clin Cancer Res. Jan. 15, 2004;10(2):440-8.
Muscato, et al. Optimal dosing of ketoconazole (KETO) and hydrocortisone (HC) leads to long responses in hormone refractory prostate cancer. Proc ASCO. 1994;229:701.
Nicolaou, et al. Natural Product-like Combinatorial Libraries Based on Privileged Structures. 1. General Principles and Solid-Phase Synthesis of Benzopyrans. J. Am. Chem. Soc. 2000; 122(41):9939-9953.
NIH Grant Project Reference No. 2RO1 CA27440-24A1, 2R01 CA27440-25A1 Revised Grant Renewal Application, approximate submission date Feb. 18, 2004; approximate award date Sep. 23, 2004.
NIH Grant Project Reference No. 3R)1 CA27440-22S1 Grant Application for Supplemental Funding, approximate date Jun. 21, 2001; approximate award date Aug. 17, 2001.
NIH Grant Project Reference No. 3RO1 CA27440-22S1 Grant Application for Supplemental Funding, approximate date Jun. 21, 2001; approximate award date Aug. 17, 2001.
NIH Grant Project Reference No. 3RO1 CA27440-23S1 Grant Continuation Application and Progress Report, approximate date May 3, 2002; approximate award date Jun. 21, 2002.
NIH Grant Project Reference No. 5R)1 CA27440-24S1 Grant Continuation Application and Progress Report, approximate date Apr. 1, 2003; approximate award date Jun. 3, 2003.
NIH Grant Project Reference No. 5RO1 CA27440-23 Grant Continuation Application and Progress Report, approximate date Jan. 21, 2002; approximate award date Apr. 29, 2002.
NIH Grant Project Reference No. 5RO1 CA27440-24 Grant Continuation Application and Progress Report, approximate date Feb. 20, 2003; approximate award date Jun. 3, 2003.
NIH Grant Project Reference No. 5RO1 CA27440-24S1 Grant Continuation Application and Progress Report, approximate date Apr. 1, 2003; approximate award date Jun. 3, 2003.
NIH Grant Project Reference No. 5RO1 CA27440-25 Grant Renewal Application, approximate submission date Jun. 26, 2003—Unfunded.
NIH Grant Project Reference No. 5RO1 CA27440-26 Grant Continuation Application and Progress Report, approximate submission date Jul. 1, 2005; approximate award date Aug. 2, 2005.
NIH Grant Project Reference No. 5RO1 CA27440-27 Grant Continuation Application and Progress Report, approximate submission date Apr. 26, 2006.
NIH Grant Project Reference No. 5RO1CA27440-27 ESNAP Report, approximate submission date May 8, 2006.

(56) References Cited

OTHER PUBLICATIONS

Njar, et al Inhibitors of 17alpha-hydroxylase/17,20-lyase (CYP17): potential agents for the treatment of prostate cancer. Curr Pharm Des. Mar. 1999;5(3):163-80.
Njar, et al. Novel 17-azolyl steroids, potent inhibitors of human cytochrome 17 alpha-hydroxylase-C17,20-1yase (P450(17) alpha): potential agents for the treatment of prostate cancer. J Med Chem. Mar. 12, 1998;41(6):902-12.
Njar, et al. Nucleophilic vinylic 'Addition-Elimination' Substitution Reaction of 3B-Acetoxy-17-Chloro-16-Formylandrosta-5,16-Diene: A Novel and General Route to 17-Substituted Steroids Bioorganic and Medical Chemistry Letters 1996; 6(22):2777-27820.
Nnane, et al. Effects of novel 17-azolyl compounds on androgen synthesis in vitro and in vivo. J Steroid Biochem Mol Biol. Dec. 15, 1999;71(3-4):145-52.
O'Donnell, et al. Hormonal impact of the 17alpha-hydroxylase/C(17,20)-lyase inhibitor abiraterone acetate (CB7630) in patients with prostate cancer. Br J Cancer. Jun. 14, 2004;90(12):2317-25.
Office Action dated Jan. 31, 2011 for U.S. Appl. No. 12/577,094.
Office Action dated Mar. 12, 2010 for U.S. Appl. No. 11/817,550.
Office Action dated May 5, 2010 for U.S. Appl. No. 12/577,091.
Office Action dated May 7, 2010 for U.S. Appl. No. 12/577,092.
Office Action dated May 23, 2011 for U.S. Appl. No. 12/577,094.
Office Action dated May 25, 2010 for U.S. Appl. No. 12/577,096.
Office Action dated Jun. 1, 2010 for U.S. Appl. No. 12/577,090.
Office Action dated Jun. 1, 2011 for U.S. Appl. No. 12/623,257.
Office Action dated Jun. 2, 2010 for U.S. Appl. No. 11/817,550.
Office Action dated Sep. 8, 2011 for U.S. Appl. No. 12/577,096.
Office Action dated Sep. 9, 2011 for U.S. Appl. No. 12/577,090.
Office Action dated Oct. 20, 2010 for U.S. Appl. No. 12/623,257.
Office Action dated Oct. 28, 2010 for U.S. Appl. No. 12/577,091.
Office Action dated Oct. 28, 2010 for U.S. Appl. No. 12/577,092.
Office Action dated Oct. 29, 2010 for U.S. Appl. No. 12/577,090.
Office Action dated Nov. 1, 2010 for U.S. Appl. No. 12/577,096.
Ojida, et al. Stereocontrolled synthesis of (1S)-1-(1H-imidazol-4-yl)-1-(6-methoxy- 2-naphthyl)-2-methylpropan-1-ol as a potent C17,20-lyase inhibitor. Tetrahedron: Asymmetry. 2004; 15L1555-1559.
Picard, et al. Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. I Med Chem. Aug. 1, 2002;45(16):3406-17.
Potter, et al. A convenient, large-scale synthesis of abiraterone acetate [3B-acetoxy-17-(3-pryidyl)androsta-5,16-diene], a potential new drug for the treatment of prostate cancer. Organic Preparations and Procedures Int. 1997; 29(1):123-134.
Potter, et al. Novel steroidal inhibitors of human cytochrome P45017 alpha (17 alpha-hydroxylase-C17,20-lyase): potential agents for the treatment of prostatic cancer. J Med Chem. Jun. 23, 1995;38(13):2463-71.
Randimbivololona, et al. Metabolism and excretion in bile of SC4453, a new semi-synthetic derivative of digoxin following an i.v. bolus injection in the guinea-pig. J. Pharmacol. Jan.-Mar. 1984;15(1):53-64.
Recanatini, et al. A new class of nonsteroidal aromatase inhibitors: design and synthesis of chromone and xanthone derivatives and inhibition of the P450 enzymes aromatase and 17 alpha-hydroxylase/C17,20-lyase. Med Chem. Mar. 1, 2001;44(5):672-80.
Ru, et al. Synthesis and Pharmacological Activity of some 17-[2'substituted)-4'- pyrimidyl] androstene derivativies as inhibitors of human 17alpha-hydroxylase/C17,20-lyse., J. Chin. Pharm. Sci., Jun. 2001, vol. 10, No. 1, pp. 3-8.
Small, et al. Ketoconazole retains activity in advanced prostate cancer patients with progression despite flutamide withdrawal. J Urol. Apr. 1997;157(4):1204-7.
Souillac, et al. Characterization of Delivery Systems, Differential Scanning Calorimetry in Encyclopedia of Controlled Drug Delivery, 1999, John Wiley & Sons, pp. 212-227.
Supplementary European Search Report dated Jul. 29, 2009 for European Application No. EP 06736460.
Thompson, et al. Androgen antagonist activity by the antioxidant moiety of vitamin E, 2,2,5,7,8-pentamethyl-6-chromanol in human prostate carcinoma cells. Mol Cancer Ther. Aug. 2003;2(8):797-803.
Tindall, et al. Symposium on androgen action in prostate cancer. Cancer Res. Oct. 1, 2004;64(19):7178-80.
Trachtenberg, et al. Ketoconazole: a novel and rapid treatment for advanced prostatic cancer. J Urol. Jul. 1983;130(1):152-3.
Vasaitis, et al. Androgen Receptor Inactivation Contributes to Antitumor Efficacy of CYP17 Inhibitor VN/124-1 in Prostate Cancer. Mol. Cancer Therapeutics. 2008;7(8):2348-2357.
Vasaitis, et al. The Effects of Novel Anti-Androgens on Androgen Receptor Action and Expression. Proceedings of the American Association for Cancer Research. 2006; 47:Abstract 5340. http://aacrmeetingabstracts.org/cgi/content/abstract/2006/1/252-d.
Vippagunta, et al. Crystalline solids. Adv Drug Deliv Rev. May 16, 2001;48(1):3-26.
Zhang, et al. A small composite probasin promoter confers high levels of prostate-specific gene expression through regulation by androgens and glucocorticoids in vitro and in vivo. Endocrinology. Dec. 2000;141(12):4698-710.
Office Action dated Apr. 4, 2012 for U.S. Appl. No. 12/577,090.
Office Action dated Oct. 17, 2012 for U.S. Appl. No. 12/577,090.
Office action dated May 30, 2013 for GB Application No. 1114154.6.

STEROIDAL CYP17 INHIBITORS/ANTIANDROGENS

CROSS-REFERENCE

This application is the National Stage of International Application No. PCT/US2010/023387, filed Feb. 5, 2010, which claims the benefit under 35 U.S.C. Sec. 119(e) of U.S. Provisional Application No. 61/150,027, filed Feb. 5, 2009, and which is incorporated herein by reference in its entirety.

FIELD OF THE INVENTION

This invention provides novel steroidal CYP17 inhibitors for the treatment of urogenital and/or androgen-related cancers, diseases and/or conditions, including castration-resistant prostate cancer. The invention also provides methods of synthesizing new chemical entities and methods of using the same in treating cancer and urogenital and/or androgen-related cancers, diseases and/or conditions.

BACKGROUND OF THE INVENTION

Prostate cancer (PCA) is the most common malignancy and age-related cause of cancer death worldwide. Apart from lung cancer, PCA is the most common form of cancer in men and the second leading cause of death in American men. In the United States in 2008, it was estimated that 186,320 new cases of prostate cancer would be diagnosed and about 28,660 men would die of this disease, with African American men and Jamaican men of African decent having the highest incidence rates in the world (American Cancer Society—Cancer Facts and Figures 2008).

Androgens play an important role in the development, growth, and progression of PCA (McConnell, J. D., *Urol. Clin. North Am.*, 1991, 18: 1-13), with the two most important androgens in this regard being testosterone (T), 90% of which is synthesized by the testes, and the rest (10%) is synthesized by the adrenal glands, and the more potent androgen, dihydrotestosterone (DHT), to which testosterone is converted by the enzyme steroid, 5α-reductase, that is localized primarily in the prostate (Bruchovsky, N. and Wilson, J. D., *J. Biol. Chem.*, 1968, 243, 2012-2021).

Huggins et al. introduced androgen deprivation as a therapy for advanced and metastatic PCA in 1941 (Huggins, C., Stephens, R. C. and Hudges, C. V., *Arch. Surg.*, 1941, 43, 209-212) and since then, androgen ablation therapy has been shown to produce the most beneficial responses in multiple settings in PCA patients (Denmeade, S. R. and Isaacs, J. T., *Nature Rev. Cancer*, 2002, 2: 389-396). Orchiectomy (either surgical or medical with a GnRH agonist), which reduces or eliminates androgen production by the testes, but does not affect androgen synthesis in the adrenal glands, is the standard treatment option for most prostate cancer patients. Several studies have reported that a combination therapy of orchiectomy with antiandrogens, to inhibit the action of adrenal androgens, significantly prolongs the survival of PCA patients (Crawford, E. D. et al, *New Engl. J. Med.*, 1989, 321, 419-424; Crawford, E. D. and Allen, J. A., *J. Urol.*, 1992, 147: 417A; and Denis, L., *Prostate*, 1994, 5 (Suppl.), 17s-22s).

In a recent featured article by Mohler and colleagues (Mohler, J. L. et al., *Clin. Cancer Res.*, 2004, 10, 440-448), it was clearly demonstrated that testosterone and dihydrotestosterone occur in recurrent PCA tissues at levels sufficient to activate androgen receptors. In addition, using microarray-based profiling of isogenic PCA xenograft models, the Sawyer group (Chen, C. D. et al., *Nat. Med.*, 2004, 10, 33-39) found that a modest increase in the androgen receptor mRNA was the only change consistently associated with the development of resistance to antiandrogen therapy. Potent and specific compounds that inhibit androgen synthesis in the testes, adrenals, and other tissue may be more effective for the treatment of PCA (Njar, V. C. O. and Brodie, A. M. H., *Current Pharm. Design*, 1999, 5: 163-180).

In the testes and adrenal glands, the last step in the biosynthesis of testosterone involves two key reactions, which act sequentially, and are both catalyzed by a single enzyme, the cytochrome P450 monooxygenase 17α-hydroxylase/$_{17,20}$-lyase (CYP17; Hall, P. F., *J. Steroid Biochem. Molec. Biol.*, 1991, 40, 527-532). Ketoconazole, an antifungal agent that also inhibits P450 enzymes, is, in addition, a modest CYP17 inhibitor, and has been used clinically for the treatment of PCA (Trachtenberg, J, et al., *Urol.* 1983, 130, 152-153). It is reported that careful scheduling of treatment can produce prolonged responses in otherwise castrate-resistant prostate cancer patients (Muscato, J. J. et al., *Proc. Am. Assoc. Cancer Res.*, 1994, 13: 22 (Abstract)). Further, ketoconazole was found to retain activity in advanced PCA patients with progression, despite flutamide withdrawal (Small, E. J. et al., *J. Urol.*, 1997, 157, 1204-1207). Although, the drug has now been withdrawn from use because of liver toxicity and other side effects, the ketoconazole results suggest that more potent and selective inhibitors of CYP17 could provide useful agents for treating this disease, even in advanced stages and in some patients who may appear to be hormone refractory.

A variety of potent steroidal and non-steroidal inhibitors of CYP17 have been reported and some have been shown to be potent inhibitors of testosterone production in rodent models. Recently, Jarman and colleagues have described the hormonal impact of their most potent CYP17 inhibitor, abiraterone, in patients with prostate cancer (O'Donnell, A. et al., *Br. J. Cancer*, 2004, 90: 2317-2325). Some potent CYP17 inhibitors have been shown to also inhibit 5α-reductase and/or be potent antiandrogens with potent antitumor activity in animal models (Long, B. J. et al., *Cancer Res.*, 2000, 60, 6630-6640).

Additional background of the invention is contained in U.S. Pat. No. 5,604,213 (Barrie et al); U.S. Pat. No. 5,994,335 (Brodie et al); U.S. Pat. No. 6,200,965 (Brodie et al); and U.S. Pat. No. 6,444,683 (Brodie et al), each of which is incorporated by reference in its entirety.

Recent publications from Barrie et al. and Njar et al. teach a class of potent steroidal CYP17 inhibitors/antiandrogens, 17-pyridines, 17-benzoazoles, 17-pyrimidinoazoles and 17-diazines, that are particularly potent as inhibitors of the human CYP17 enzyme. Particularly-potent CYP17 inhibitors include 3β-hydroxy-17-(pyrid-3-yl)androsta-5,16-diene (abiraterone), 3β-hydroxy-17-(1H-benzimidazole-1-yl)androsta-5,16-diene (Compound 1), 17-(1H-benzimidazole-1-yl)androsta-4,16-diene-3-one (Compound 2) and 3β-hydroxy-17-(5'-pyrimidyl)androsta-5,16-diene (Compound 3), with IC$_{50}$ values of 3-6, 50, 915, and 500 nM, respectively.

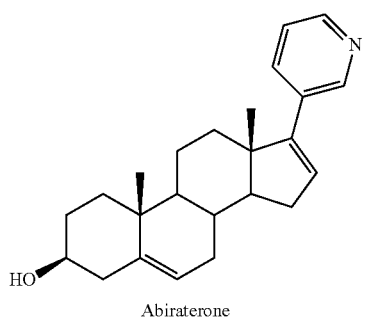

Abiraterone

-continued

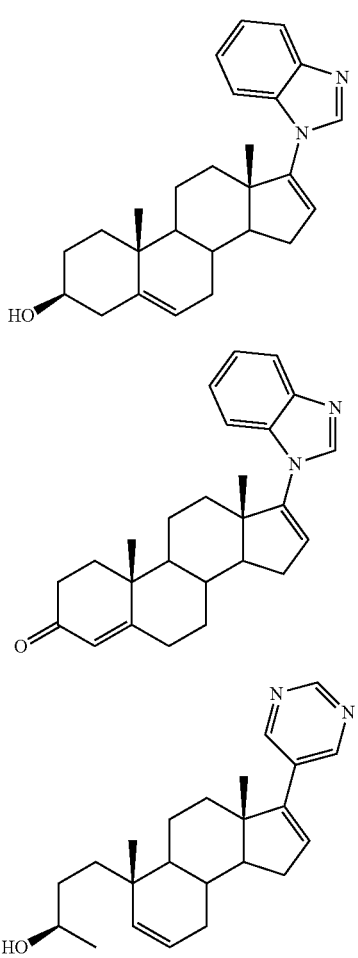

Compound 1

Compound 2

Compound 3

Compounds 1, 2, and 3 were effective at competing with the binding of $^3$H-R1881 (methyltrienolone, a stable synthetic androgen) to both the mutant and LNCaP AR and the wild-type AR, but with a 2.2- to 5-fold higher binding efficiency to the latter. Compounds 1 and 2 were also shown to be potent pure AR antagonists, and cell growth studies have shown that they also inhibit the growth of DHT-stimulated LNCaP and LAPC4 prostate cancer cells, with $IC_{50}$ values in the low micromolar range (i.e., <10 μM). Their inhibitory potencies were comparable to that of casodex, but remarkably superior to that of flutamide. The pharmacokinetics of compounds 1 and 2 in mice showed that following s.c. administration of 50 mg/kg of compounds 1 and 2, peak plasma levels of 16.82 and 5.15 ng/mL, respectively, occurred after 30-to-60 minutes, both compounds were cleared rapidly from plasma (terminal half-lives of 44.17 and 39.93 min, respectively) and neither was detectable at 8 hours.

Compound 1 was rapidly converted into a metabolite, tentatively identified as 17-(1H-benzimidazol-1-yl)androsta-3-one. When tested in vivo, compound 1 proved to be very effective at inhibiting the growth of androgen-dependent LAPC4 human prostate tumor xenograft, while compound 2 was ineffective. Administration of compound 1 (50 mg/kg, twice daily) resulted in a 93.8% reduction (P=0.00065) in the mean final tumor volume compared with controls, and it was also significantly more effective than castration. This was the first example of an anti-hormonal agent (an inhibitor of androgen synthesis (CYP17 inhibitor)/antiandrogen) that is significantly more effective than castration in suppression of androgen-dependent prostate tumor growth. In view of these impressive anti-cancer properties, compound 1 and analogs may be used for the treatment of urogenital and/or androgen-related cancers, diseases and/or conditions, including but not limited to, human prostate cancer, as well as breast cancer, ovarian cancer, and other urogenital cancers.

SUMMARY OF THE INVENTION

In some embodiments, the invention contemplates a compound of Formula I:

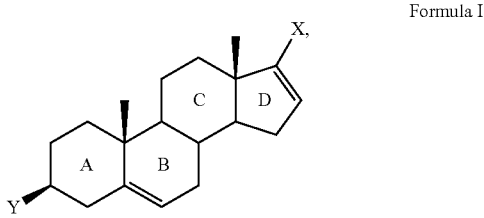

Formula I wherein: each position of the ABC ring structure is independently optionally substituted; X is an aromatic group comprising at least 2 fused rings, a 10-electron aromatic system, and at least one nitrogen ring atom capable of coordinating a heme group of CYP17, wherein X is not benzimidazole; and Y is OH, an ester, or a prodrug group, or a pharmaceutically-acceptable salt or analog thereof.

In some embodiments, the invention contemplates a pharmaceutical composition comprising a therapeutically-effective amount of one or more compounds of Formula I and one or more pharmaceutically-acceptable excipients, bulking agents, binders, flow agents, release agents, carriers or diluents.

In some embodiments, the invention contemplates a method of treating a cancer in a subject in need or want thereof, the method comprising administering to the subject a therapeutically-effective amount of a compound of Formula I.

In some embodiments, the invention contemplates a method of treating cancer in a subject in need or want thereof, the method comprising administering to the subject a therapeutically-effective amount of a compound of Formula I, in combination with a hormone therapy, a chemotherapy, a radiation therapy, an immunotherapy, or surgery.

DETAILED DESCRIPTION OF THE INVENTION

As used herein, and unless otherwise defined, the following terms have the following meanings:

"alkyl" is a, $C_1$-$C_{12}$-straight-, $C_1$-$C_{12}$-branched, or $C_1$-$C_{12}$-cyclic carbon group, any of which is optionally substituted independently at each position with hydroxyl, methoxy, ethoxy, sulfhydryl, methyl mercapto, ethylmercapto, fluorine, chlorine, bromine, iodine, aryl, or heteroaryl;

"aryl" is a mono- or polycyclic aromatic system. Non-limiting examples or aryl include phenyl, naphthyl, indenyl, fluorenyl, phenathrenyl, or azulenyl. In some embodiments, an aryl group is a 10-electron aromatic system. Aryl is optionally substituted independently at each position with hydroxyl, methoxy, ethoxy, sulfhydryl, methylmercapto, ethylmercapto, fluorine, chlorine, bromine, iodine, and heteroaryl. In some embodiments, the aryl ring system contains from five to ten carbon atoms;

"heteroaryl" is a mono- or polycyclic aromatic system comprising at least one aromatic ring with at least one ring heteroatom, wherein the heteroatom is nitrogen, oxygen, or sulfur. Heteroaryl is optionally substituted independently at each position with hydroxyl, methoxy, ethoxy, sulfhydryl, methyl mercapto, ethylmercapto, fluorine, chlorine, bromine, iodine, oxo and aryl. Non-limiting examples of heteroaryl groups include furan, thiophene, pyrrole, pyrrazole, imidazole, oxazole, isoxazole, thiazole, isothiazole, triazole, thiadiazole, oxadiazole, pyridine, pyrimidine, pyrazine, pyridazine, triazine, indole, carbazole, benzofuran, benzothiphene, benzthiazole, indazole, quinoline, isoquinoline, cinnoline, and phthalazine. In some embodiments, heteroaryl groups contain from five to twelve ring atoms; and "alkylaryl" refers to an alkyl group that is distally attached via an aryl group, for example, o-, m-, or p-toluyl.

Numbering of the steroid core as used herein is:

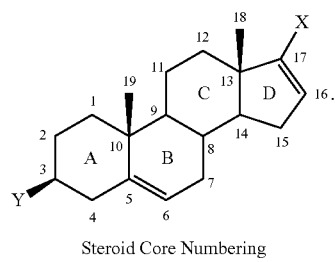

Steroid Core Numbering

The 1-azaazulen-3-yl, 2-alkylindazol-3-yl, pyrazolo-[1,5-a]-pyridin-3-yl, imidazo-[1,2-a]-pyridin-3-yl, pyrazolo-[2,3-a]-pyrimidin-3-yl, pyrazolo-[2,3-c]-pyrimidin-3-yl, imidazo-[1,2-c]-pyrimidin-3-yl, imidazo-[1,2-a]-pyrimidin-3-yl, 4-alkylpyrazolo-[1,5-a]imidazol-3-yl, 2,1-benzoxazol-3-yl, 2,1-benzthiazol-3-yl, imidazo[2,1-b][1,3]oxazol-5-yl, or imidazo[2,1-b][1,3]thiazol-5-yl, imidazo-[2,1-b][1,2]isoxazol-6-yl, structures are the following structures, respectively:

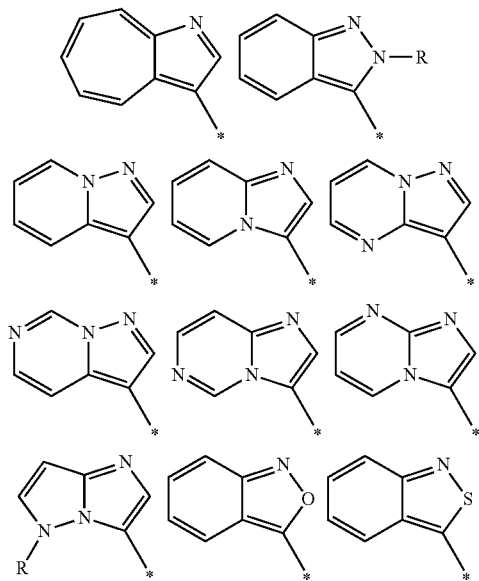

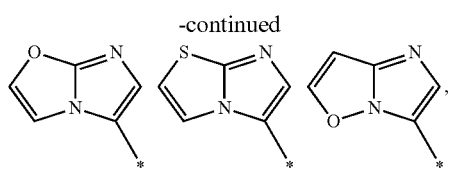

wherein the * is the point of attachment, and R is $C_1$-$C_6$-alkyl, alkoxyalkyl, alkylaryl, aryl or heteroaryl.

In one embodiment, the C ring substitution consists of the C13 methyl group.

In some embodiments a 3-β-hydroxyl group is the only heteroatom substitution on the steroid core.

In some embodiments, the compound is:

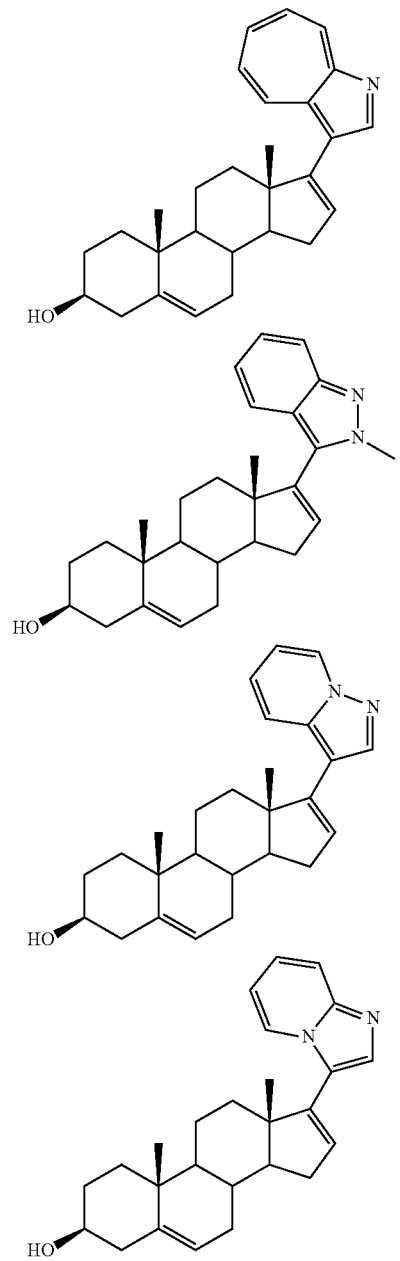

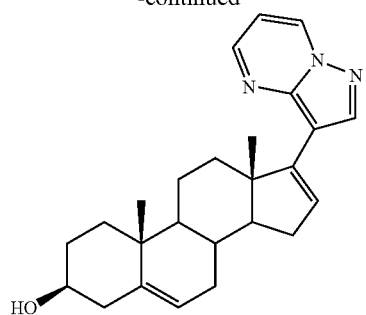
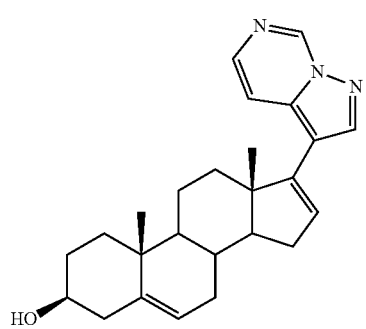
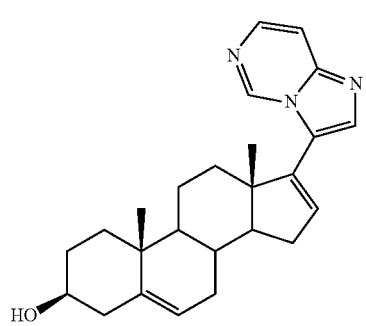
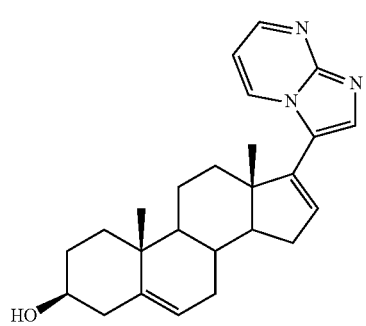
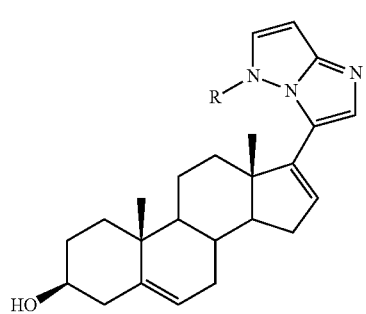
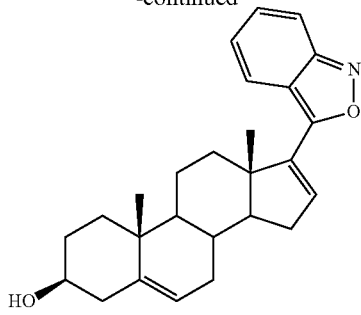
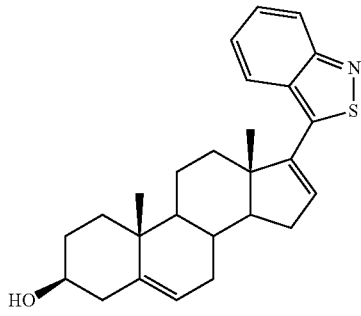
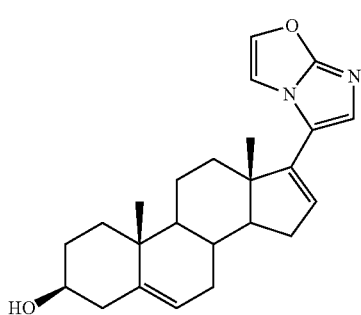
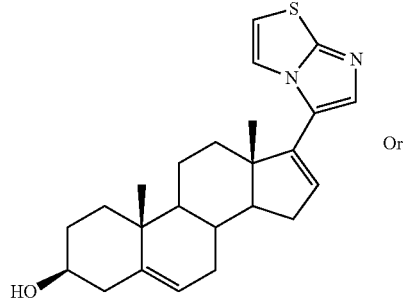
Or
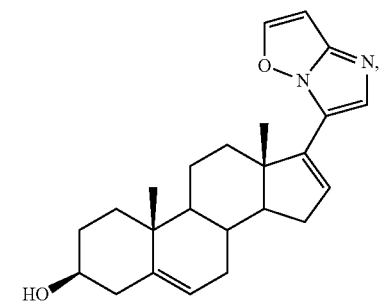
wherein R is $C_1$-$C_6$-alkyl, alkoxyalkyl, alkylaryl, aryl or heteroaryl.

In some embodiments, the compounds of the invention include 17-(1-azaazulen-3-yl)androsta-5,16-dien-3β-ol; 17-(2-alkylindazol-3-yl)androsta-5,16-dien-3β-ol; 17-(pyrazolo-[1,5-a]-pyridin-3-yl)androsta-5,16-dien-3β-ol; 17-(imidazo-[1,2-a]-pyridin-3-yl)androsta-5,16-dien-3β-ol; 17-(pyrazolo-[2,3-a]-pyrimidin-3-yl)androsta-5,16-dien-3β-ol; 17-(pyrazolo-[2,3-c]-pyrimidin-3-yl)androsta-5,16-dien-3β-ol; 17-(imidazo-[1,2-c]-pyrimidin-3-yl)androsta-5,16-dien-3β-ol; 17-(imidazo-[1,2-a]-pyrimidin-3-yl)androsta-5,16-dien-3β-ol; 17-(4-alkylpyrazolo-[1,5-a]imidazol-3-yl)androsta-5,16-dien-3β-ol; 17-(2,1-benzoxazol-3-yl)androsta-5,16-dien-3β-ol; 17-(2,1-benzthiazol-3-yl)androsta-5,16-dien-3β-ol; 17-(imidazo[2,1-b][1,3]oxazol-5-yl)androsta-5,16-dien-3β-ol; 17-(imidazo[2,1-b]1,3]thiazol-5-yl)androsta-5,16-dien-3β-ol; 17-(imidazo-[2,1-b][1,2]isoxazol-6-yl)androsta-5,16-dien-3β-ol; 17-(cyclopenta[b]pyrrol-3-yl)androsta-5,16-dien-3β-ol and 3-esters, metabolites, analogs, derivatives and pharmaceutically-acceptable salts thereof.

In some embodiments, the compound of this invention includes a pharmaceutically-acceptable prodrug group at the Y position of the compound of Formula I. A compound comprising a prodrug group is a prodrug. Fragmentation of the prodrug group provides a drug. In some embodiments, the drug is a 3-hydroxy compound. The 3-hydroxy compound is a compound comprising a hydroxyl group at the 3-position of the steroid core of the 3-hydroxy compound.

In some embodiments, prodrug groups provide improved oral bioavailability and pharmacokinetics. In some embodiments, the prodrug binds CYP17. In some embodiments, the prodrug does not bind CYP17. In some embodiments, the prodrug inhibits CYP17 less effectively than the drug.

The instant invention contemplates prodrug variants of any compound described herein. Non-limiting examples of prodrugs of the invention include:

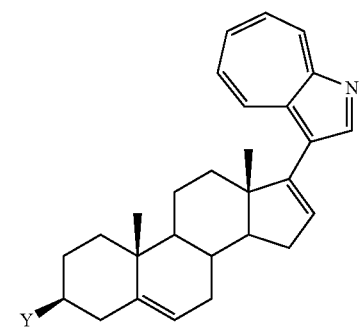

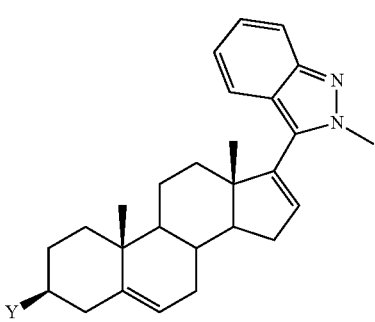

-continued

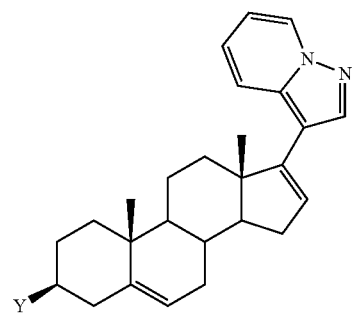

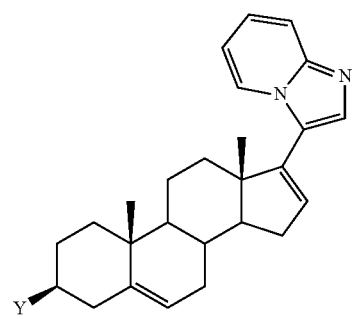

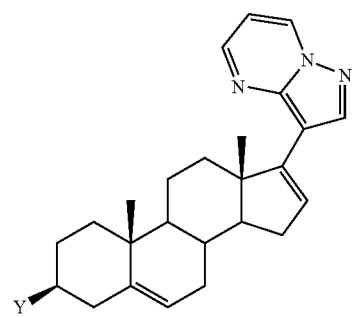

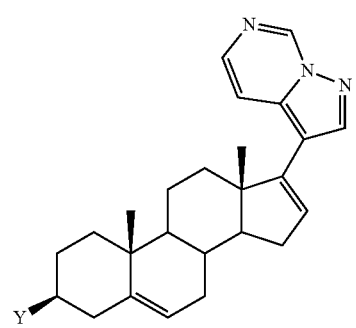

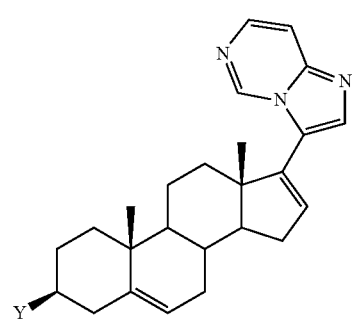

-continued
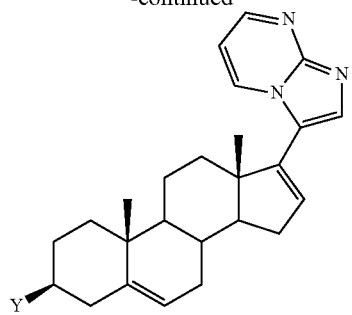
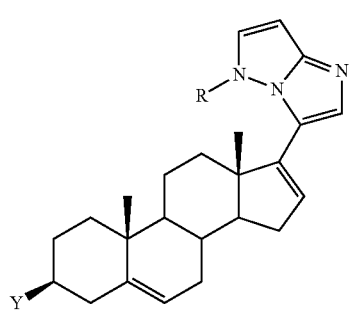
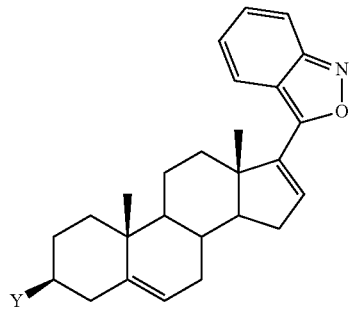
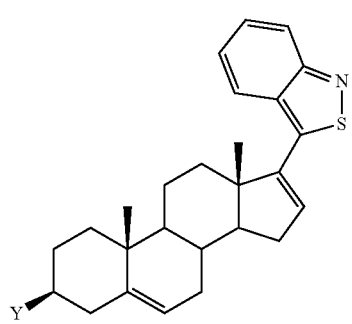
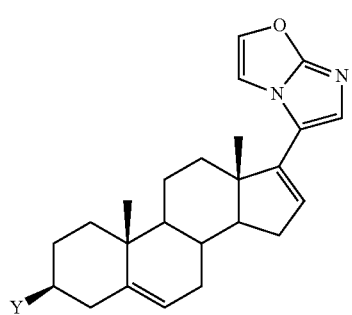
-continued
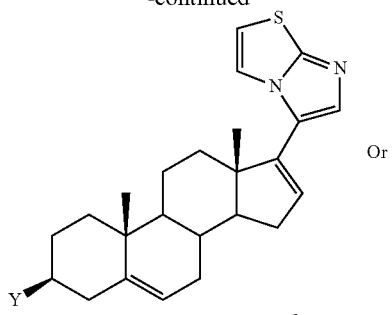
Or
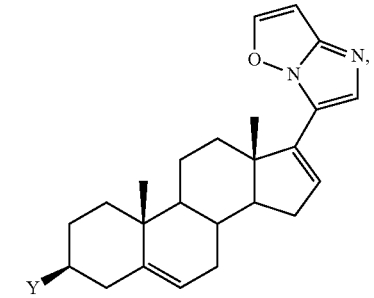
wherein Y is a prodrug group, such as cocamidopropyl betaine (CAPB), acetyl, propionyl, betaine, carnitine, cocamidopropyl betaine (CAPB), an amino acid residue or a peptidyl residue, and R is $C_1$-$C_6$-alkyl, alkoxyalkyl, alkylaryl, aryl or heteroaryl.
In some embodiments, the prodrug is:
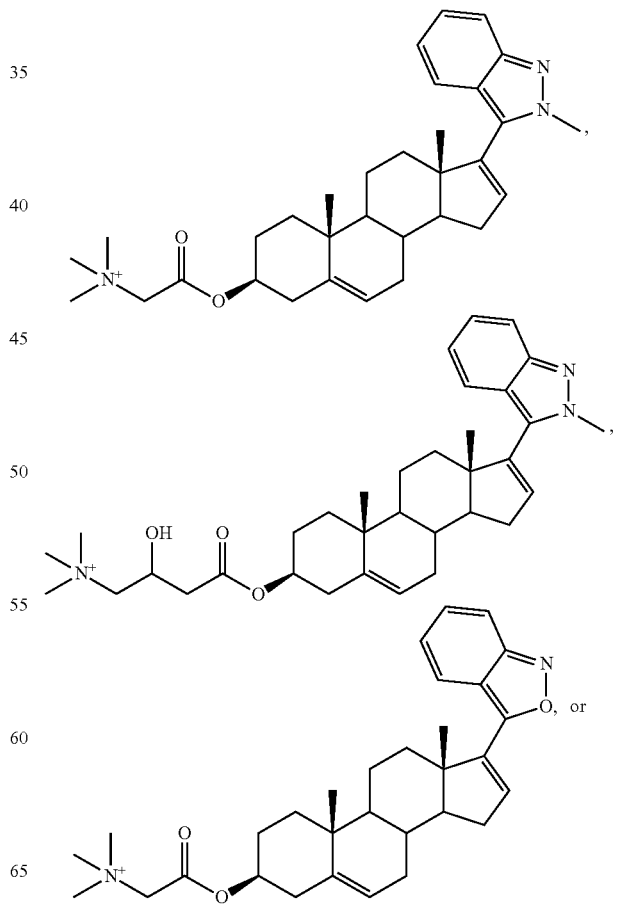

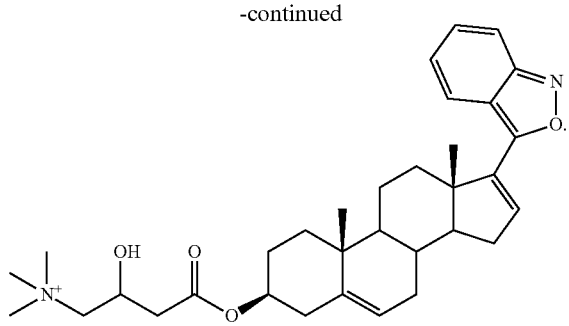

In some embodiments, a prodrug is susceptible to fragmentation under one or more sets of physiological conditions. In some embodiments, a prodrug is capable of fragmenting under one or more sets of physiological conditions. In some embodiments, a prodrug is capable of providing a 3-hydroxy compound under one or more sets of physiological conditions. In some embodiments, a prodrug is capable of providing a 3-hydroxy compound in vivo.

In some embodiments, a prodrug group is susceptible to fragmentation under one or more sets of physiological conditions. In some embodiments, a prodrug group is capable of fragmenting under one or more sets of physiological conditions. In some embodiments, a prodrug group is capable of providing a 3-hydroxy compound under one or more sets of physiological conditions. In some embodiments, a prodrug is a physiological precursor of a 3-hydroxy compound. In some embodiments, a prodrug is capable of providing a 3-hydroxy compound in vivo.

In some embodiments, a prodrug group is a physiological precursor of a hydroxyl group. In some embodiments, a physiological precursor of a hydroxyl group is a group that is capable of being converted to a hydroxyl group under one or more sets of physiological conditions. In some embodiments, a physiological precursor of a hydroxyl group is capable of providing a hydroxy compound under one or more sets of physiological conditions. In some embodiments, a physiological precursor of a hydroxyl group is capable of providing a 3-hydroxy compound under one or more sets of physiological conditions. In some embodiments, a physiological precursor of a hydroxyl group is a physiological precursor of a 3-hydroxy compound. In some embodiments, a physiological precursor of a hydroxyl group is a physiological precursor of a 3-hydroxyl group. In some embodiments, a physiological precursor of a hydroxyl group is capable of providing a 3-hydroxy compound in vivo.

In some embodiments, a prodrug group is cocamidopropyl betaine (CAPB), OAc, O-propionyl, O-betaine, O-carnitine, an amino acid group, or a peptidyl group. In some embodiments, a physiological precursor to a hydroxyl group is OAc, O-propionyl, O-betaine, O-carnitine, an amino acid group, or a peptidyl group.

In some embodiments, the set of physiological conditions that fragment a prodrug, a prodrug group, or a physiological precursor of a hydroxyl group are general. In some embodiments, the physiological conditions that fragment a prodrug, a prodrug group, or a physiological precursor of a hydroxyl group are specific to the identity of the prodrug, the prodrug group, or the physiological precursor of a hydroxyl group. In some embodiments, the physiological conditions comprise pH. In some embodiments, the physiological conditions comprise temperature. In some embodiments, the physiological conditions comprise metabolism. In some embodiments, the physiological conditions comprise hydrolysis. In some embodiments, the physiological conditions comprise catalysis. In some embodiments, the physiological conditions comprise enzyme activity. In some embodiments, the physiological conditions comprise oxidation or reduction. One non-limiting example of providing a 3-hydroxy compound is provided herein:

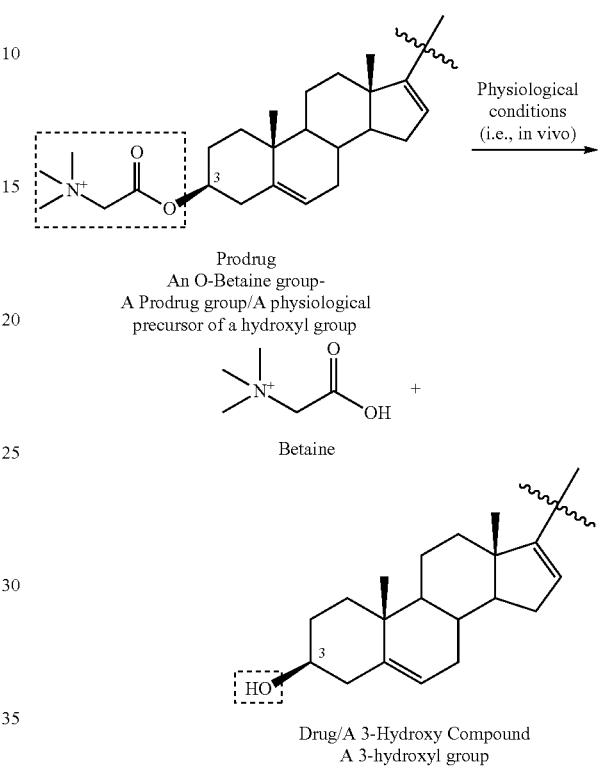

In some embodiments, a compound of the invention binds a heme group of CYP17. In some embodiments, the heme group is in the active site of CYP17. In some embodiments, the compound binds the heme group via a lone pair of electrons. In some embodiments, the lone pair of electrons is on a nitrogen atom. In some embodiments, the nitrogen atom is a ring atom of the $C_{17}$ group. In some embodiments, the nitrogen atom is in a 5-membered ring. In some embodiments, the nitrogen atom is gamma to the 17-position of the D-ring. In some embodiments, the nitrogen atom is three heavy atoms away from the 17-position of the D-ring. In some embodiments, the nitrogen atom is 1,4-to the 17-position of the D-ring. In some embodiments, the nitrogen is at the 1-position of the $C_{17}$ group.

In some embodiments, the $C_{17}$ group is substituted with an alkyl group. In some embodiments, the alkyl group modifies the pharmacokinetics of the compound. In some embodiments, the alkyl group modifies the inhibitory activity of the compound. In some embodiments, the alkyl group optimizes the biological activity of the compound. In some embodiments, a nitrogen-containing heterocycle comprises tautomers. In some embodiments, an alkyl group on a nitrogen ring atom in the $C_{17}$ heterocycle eliminates a tautomeric form, thereby disposing an electron lone pair on a desired nitrogen atom. In some embodiments, one tautomeric form of a compound is characterized by greater biological activity than another tautomeric form of the same compound.

In some embodiments, substituents on the $C_{17}$ heterocycle modify the steric and/or electronic properties of the compound. In some embodiments, the biological activity of a compound is improved by modifying the steric and/or electronic properties of the compound.

In some embodiments the off rate of the compound is low, thereby practically eliminating the enzymatic activity of CYP17. In some embodiments, the off rate of the compound is lowered by modifying the steric and electronic properties of the compound.

Some embodiments contemplate pharmaceutically-acceptable salts of the invention. Pharmaceutically-acceptable salts of the compounds of the invention are generated, for example, by treating the compounds of the invention with an acid, a hemi-acid, or a salt to afford the corresponding salt form. Non-limiting examples of pharmaceutically-acceptable salts include chlorides, bromides, iodides, phosphates, sulfates, carbonates, bicarbonates, formates, acetates, propionates, benzoates, picolinates, fumarates, maleates, malates, succinates, methanesulfonates, toluenesulfonates, mesitylenesulfonates, trifluoromethanesulfonates, tetrafluoroborates, tetraphenylborates, and hexafluorophosphates.

In some embodiments, the invention contemplates a pharmaceutical composition comprising one or more compounds of the invention. In some embodiments, a pharmaceutical composition further comprises a pharmaceutically-acceptable carrier, for example, vehicles, adjuvants, excipients, and/or diluents that are well-known to those skilled in the art. The choice of carrier will be determined, in part, by the particular composition desired and by the particular method used to administer the composition. Accordingly, there are a wide variety of suitable formulations of the pharmaceutical compositions contemplated by the present invention.

The present invention also relates to a method of treating urogenital and/or androgen-related cancers, diseases or conditions, including, without limitation, breast cancer, prostate cancer, and other urogenital cancers, benign prostatic hyperplasia, or other androgen-related diseases and/or conditions, by administering to a subject in need thereof a therapeutically-effective amount of a compound in accordance with the present invention. The treatment may be prophylactic (referring to any degree of inhibition of the onset of a cellular disorder, including complete inhibition, such as in a subject expected to soon exhibit the cellular disorder) or therapeutic (referring to any degree of inhibition or any degree of beneficial effects on the disorder or condition in the subject (e.g., human), e.g., inhibition of the growth or metastasis of a tumor or circulating tumor cells). Maintenance therapy, in which continued suppression of symptoms or progression of disease is achieved by continued administration of the compound, is also contemplated by this invention. Examples of prostate diseases that can be treated include, e.g., prostatic hyperplasia (BPH), and prostate cancer (e.g., prostatic adenocarcinoma).

Non-limiting examples of cancer symptoms include: tumors, persistent cough, bloody saliva, changes in bowel habits, bloody stool, anemia, lumps including lumps of the breast or testicle, bodily discharges, changes in urinary habits, pain or burning upon urination, prostate enlargement, bloody urine, swollen glands, warts, moles, genital bleeding, involuntary weight gain or loss, persistent itching, persistent skin discoloration, non-healing sores, headaches, pain or discomfort such as in the back or pelvis, cramps such as abdominal cramps, weakness, and loss of appetite.

Suitable methods of administering a compound of the present invention to a subject, for example, a mammal, such as a rat, rabbit, dog or human, are known in the art. Although more than one route may be used to administer a particular composition, a particular route can provide a more immediate and more effective result than another route.

In some embodiments, a pharmaceutical composition is formulated for oral administration. In some embodiments, the composition comprises a suspension of a compound in a suitable vehicle. Non-limiting examples of vehicles for oral administration include phosphate-buffered saline (PBS), 5% dextrose in water (D5W) and a syrup. In some embodiments, a composition is formulated to stabilize the consistency of a dose over a period of storage and administration. In some embodiments, the composition comprises a solution. In some embodiments, a solution comprises an effective amount of one or more compounds dissolved in a diluent. Non-limiting examples of diluents include water, saline, and buffers. In some embodiments, the composition comprises a solid dosage form. In some embodiments, the solid dosage form comprises a capsule, a caplet, a lozenge, a sachet, or a tablet. In some embodiments, the solid dosage form is a liquid-filled dosage form. In some embodiments, the solid dosage form is a solid-filled dosage form. In some embodiments, the solid dosage form is a solid-filled tablet, capsule, or caplet. In some embodiments, the solid-filled dosage form is a powder-filled dosage form. In some embodiments, the solid dosage form comprises a compound in the form of micronized particles, solids or granules. In some embodiments, the composition comprises an emulsion. In some embodiments, the emulsion comprises a compound of the invention characterized by surfactant properties. In some embodiments, the emulsion comprises a compound of the invention characterized by surfactant properties, wherein the compound is a prodrug.

In some embodiments, the solid dosage form comprises one or more of lactose, sorbitol, maltitol, mannitol, cornstarch, potato starch, microcrystalline cellulose, hydroxypropyl cellulose, acacia, gelatin, colloidal silicon dioxide, croscarmellose sodium, talc, magnesium stearate, stearic acid, pharmaceutically-acceptable excipients, colorants, diluents, buffering agents, moistening agents, preservatives, flavoring agents, carriers, and binders. In some embodiments, the solid dosage form comprises one or more materials that facilitate manufacturing, processing or stability of the solid dosage form. In some embodiments, a lozenge comprises a flavoring agent. Non-limiting examples of flavoring agents include sucrose, gum acacia, gum tragacanth, a pastille, an inert base, a gelatin, glycerin, a sucrose emulsion, an acacia emulsion, and a gel. In some embodiments, a solid dosage form is coated. In some embodiments, the coating improves absorption of the compound in the gastrointestinal tract. Non-limiting examples of coatings include cellulose acetate phthalate (CAP), polyvinyl acetate phthalate (CVAP), and modified coatings thereof.

In some embodiments, the composition is formulated as an aerosol. In some embodiments, the aerosol is administered via inhalation. In some embodiments, the aerosol comprises one or more propellants. Non-limiting examples of propellants include dichlorodifluoromethane, hydrofluorocarbon (such as HFC 134a and/or 227), and nitrogen.

In some embodiments, a compound is administered by a route that is oral, parenteral, enteral, intraperitoneal, topical, transdermal, ophthalmic, nasal, local, non-oral, aerosol, spray, inhalation, subcutaneous, intravenous, intramuscular, buccal, sublingual, rectal, vaginal, intra-arterial, or intrathecal. In some embodiments, a dose is administered by a route that is oral, parenteral, enteral, intraperitoneal, topical, transdermal, ophthalmic, nasal, local, non-oral, aerosol, spray, inhalation, subcutaneous, intravenous, intramuscular, buccal, sublingual, rectal, vaginal, intra-arterial, or intrathecal. In some embodiments, the compound is administered as a suspension in PBS, D5W, or a carbohydrate-based syrup. In some embodiments, the dose is administered as a suspension in PBS, D5W, or a carbohydrate-based syrup.

In some embodiments, a dose administered to a subject is an effective dose. In some embodiments, the effective dose provides a therapeutic response in the subject within a therapeutically-useful time frame. In some embodiments, the effective dose comprises a therapeutically-effective amount of a compound. In some embodiments, the therapeutically-effective amount provides a therapeutic response in the subject within a therapeutically-useful time frame. The specific dose level and frequency of dosage are influenced by a variety of factors, including the activity, metabolic stability, bioavailability, rate of excretion, biological half-life, and mode and time of administration of the compound; the age, body weight, health condition, gender, diet, and physical and health characteristics of the subject; and the severity of the cancer or other disease or condition.

Any effective amount of the compound may be administered. In some embodiments, a dose comprises an effective amount of a compound. In some embodiments, a dose is administered once a day. In some embodiments, a dose is administered more than once a day. In some embodiments, a dose is greater than about 1 mg/day. In some embodiments, a dose is greater than about 5 mg/day. In some embodiments, a dose is greater than about 10 mg/day. In some embodiments, a dose is greater than about 25 mg/day. In some embodiments, a dose is greater than about 50 mg/day. In some embodiments, a dose is greater than about 100 mg/day. In some embodiments, a dose is less than about 5000 mg/day. In some embodiments, a dose is less than about 4000 mg/day. In some embodiments, a dose is less than about 3000 mg/day. In some embodiments, a dose is less than about 2500 mg/day. In some embodiments, a dose is less than about 2000 mg/day. In some embodiments, a dose is less than about 1500 mg/day. In some embodiments, a dose is less than about 2000 mg/day. In some embodiments, a dose is less than about 500 mg/day. In some embodiments, a dose is from about 1 mg to about 5000 mg per day. In some embodiments, a dose is from about 5 mg to about 4000 mg per day. In some embodiments, a dose is from about 10 mg to about 3000 mg per day. In some embodiments, a dose is from about 25 mg to about 2000 mg per day. In some embodiments, a dose is from about 50 mg to about 2500 mg per day. In some embodiments, a dose is from about 100 mg to about 2000 mg per day. In some embodiments, a dose is from about 100 mg to about 1000 mg per day. In some embodiments, a dose is from about 500 mg to about 1500 mg per day.

In one embodiment, a dose is about 0.01 to about 100 mg/kg of subject body mass per day. In some embodiments, a dose is about 0.05 to about 50 mg/kg of subject body mass per day. In some embodiments, a dose is about 0.1 to about 40 mg/kg of subject body mass per day. In some embodiments, a dose is about 0.25 to about 30 mg/kg of subject body mass per day. In some embodiments, a dose is about 0.5 to about 20 mg/kg of subject body mass per day. In some embodiments, a dose is about 0.75 to about 15 mg/kg of subject body mass per day. In some embodiments, a dose is about 1 to about 10 mg/kg of subject body mass per day. In some embodiments, a dose is about 2 to about 5 mg/kg of subject body mass per day.

In some embodiments, a composition has a concentration of greater than about 0.01% of the compound by mass. In some embodiments, a composition has a concentration of greater than about 0.025% of the compound by mass. In some embodiments, a composition has a concentration of greater than about 0.05% of the compound by mass. In some embodiments, a composition has a concentration of greater than about 0.075% of the compound by mass. In some embodiments, a composition has a concentration of greater than about 0.1% of the compound by mass. In some embodiments, a composition has a concentration of less than about 25% of the compound by mass. In some embodiments, a composition has a concentration of less than about 20% of the compound by mass. In some embodiments, a composition has a concentration of less than about 15% of the compound by mass. In some embodiments, a composition has a concentration of less than about 10% of the compound by mass. In some embodiments, a composition has a concentration of less than about 7.5% of the compound by mass. In some embodiments, a composition has a concentration of less than about 5% of the compound by mass. In some embodiments, a composition has a concentration of less than about 3% of the compound by mass. In some embodiments, a composition has a concentration of about 0.01% to about 25% of the compound by mass. In some embodiments, a composition has a concentration of about 0.025% to about 20% of the compound by mass. In some embodiments, a composition has a concentration of about 0.05% to about 15% of the compound by mass. In some embodiments, a composition has a concentration of about 0.02% to about 5% of the compound by mass. In some embodiments, a composition has a concentration of about 0.1% to about 3% of the compound by mass.

In some embodiments, a compound of the invention is used in combination with one or more other treatments for the cancer, disease and/or condition being treated. Non-limiting examples of treatments include hormone therapy, chemotherapy, radiation therapy, immunotherapy, and/or surgery.

In some embodiments, one or more compounds described herein are used in combination with one or more additional therapeutic agents. In some embodiments, the additional therapeutic agent is a drug. In some embodiments, the additional therapeutic agent is a hormone. Non-limiting examples of drugs and hormones for use in combination with compounds of the invention include anti-androgens, such as flutamide and nilutamide; CYP17 inhibitors, such as abiraterone; luteinizing hormone-releasing hormone agonists, such as leuprolide, goserelin and buserelin; drugs preventing the adrenal glands from making androgens, such as ketoconazole and aminoglutethimide; and estrogens. Non-limiting examples of cancer drugs include cyclophosphamide, methotrexate, Adrucil® 5-fluorouracil (5-FU), doxorubicin, carboplatin, carmustine, chlorambucil, cisplatin, cyclophosphamide, dacarbazine, ifosfamide, mechlorethamin, melphalan, procarbazine, bleomycin, doxorubicin, idarubicin mitoxantrone, chlorodeoxyadenosine, cytarabine, fludarabine, 6-mercaptopurine, methotrexate, 6-thioguanine, pentostatin, etoposide, gemcitabine, steroid creams, corticosteroids, prednisone, and dexamethasone.

Compounds of this invention may be administered to a subject at any time, as determined by the treating physician. In some embodiments, the compound is administered during one or more of Stage II, Stage III, and Stage IV of the cancer. In some embodiments, the compound is administered during an advanced stage of a urogenital and/or androgen-related disease or condition.

The embodiments of the disclosure are provided for the purpose of illustration, not limitation.

In some embodiments, the invention provides a compound of Formula I:

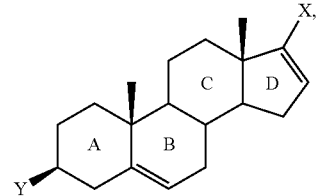

Formula I wherein:
  each position of the ABC ring structure is independently optionally substituted;
  X is an aromatic group comprising at least 2 fused rings, a 10-electron aromatic system, and at least one nitrogen ring atom capable of coordinating a heme group of CYP17, wherein X is not benzimidazole; and
  Y is OH, an ester, or a prodrug group,
or a pharmaceutically-acceptable salt or analog thereof
  In some embodiments, each position of the ABC ring structure is independently optionally substituted with one or more of alkyl, halogenated alkyl, alkenyl, halogenated alkenyl, halogen, amino, aminoalkylene, hydroxyimino, and hydroxy; and X is:

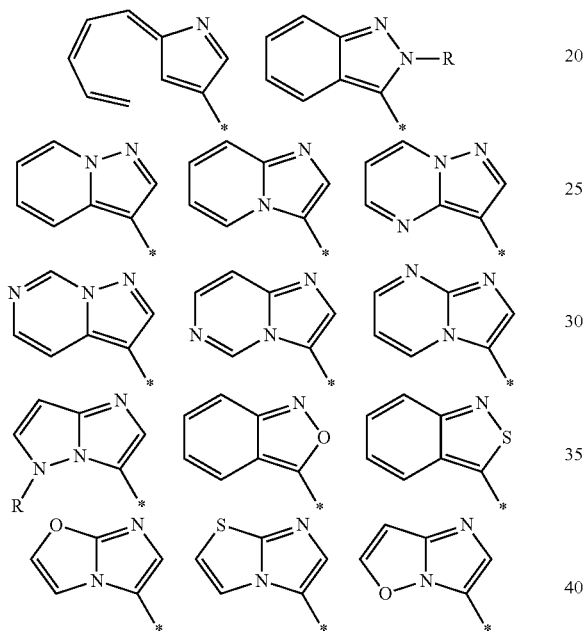

wherein * is the point of attachment, and R is $C_1$-$C_6$-alkyl, and wherein any of the foregoing groups are optionally substituted.

In some embodiments, X is optionally substituted with one or more of halogen, amino, aminoalkylene, hydroxy, —SH, —S-alkyl, alkyl and halogenated $C_1$-$C_6$-alkyl.

In some embodiments, Y is OH.

In some embodiments, the compound has the structure:

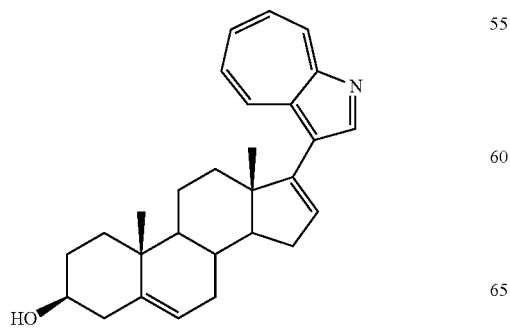

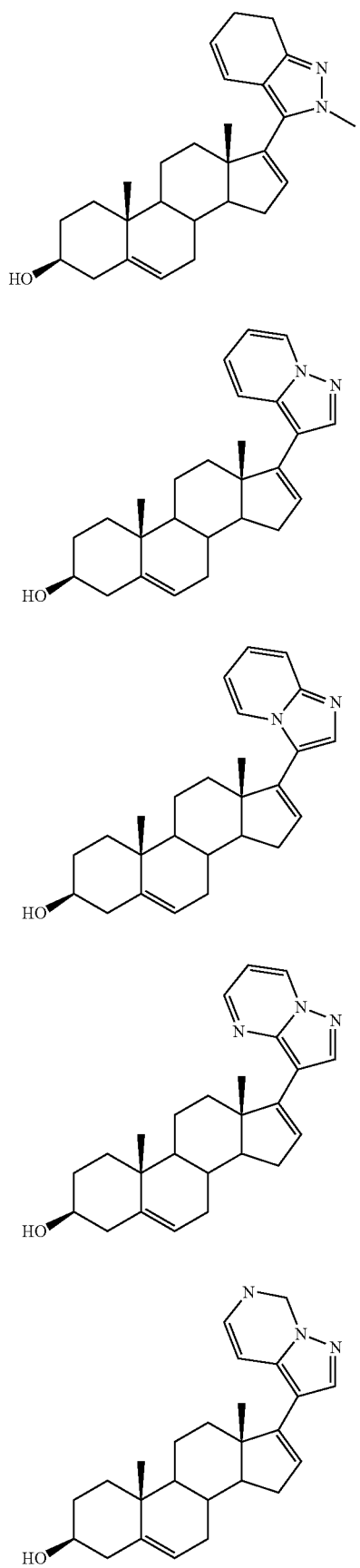

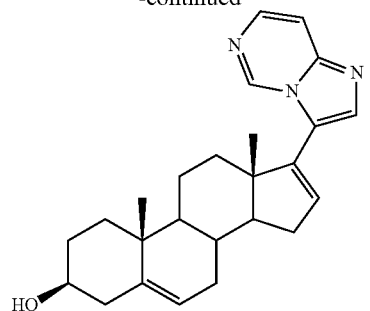
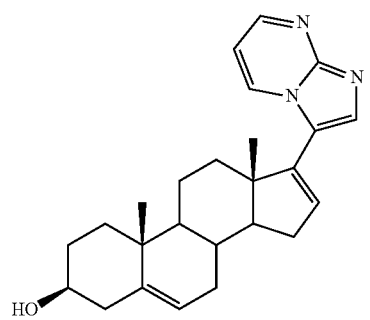
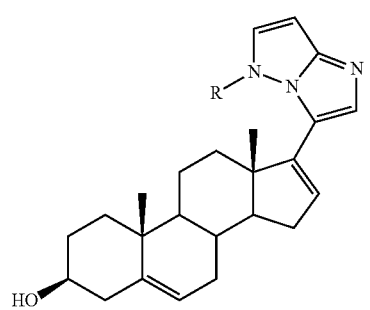
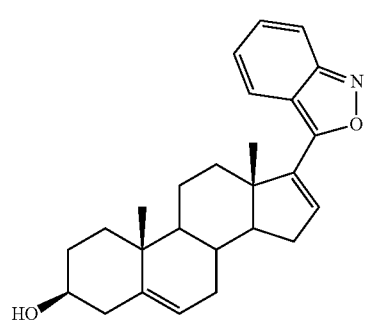
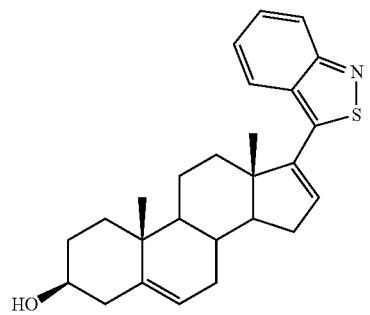
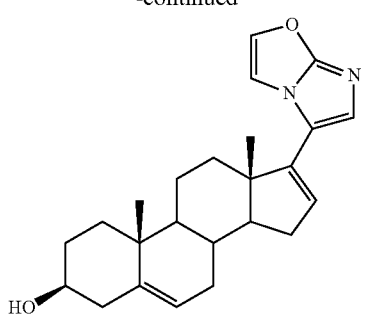
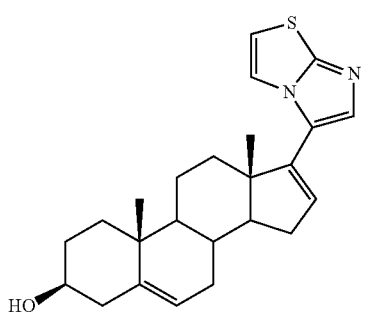
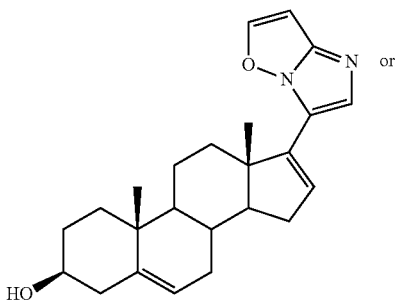
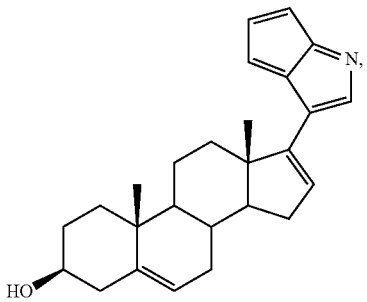
wherein R is $C_1$-$C_6$-alkyl, alkoxyalkyl, alkylaryl, aryl or heteroaryl.
In some embodiments, Y is a physiological precursor of a 3-hydroxyl group.
In some embodiments, Y is O-acetyl, O-propionyl, O-betaine, O-carnitine, an amino acid group, or a peptidyl group.

In some embodiments, the compound is:

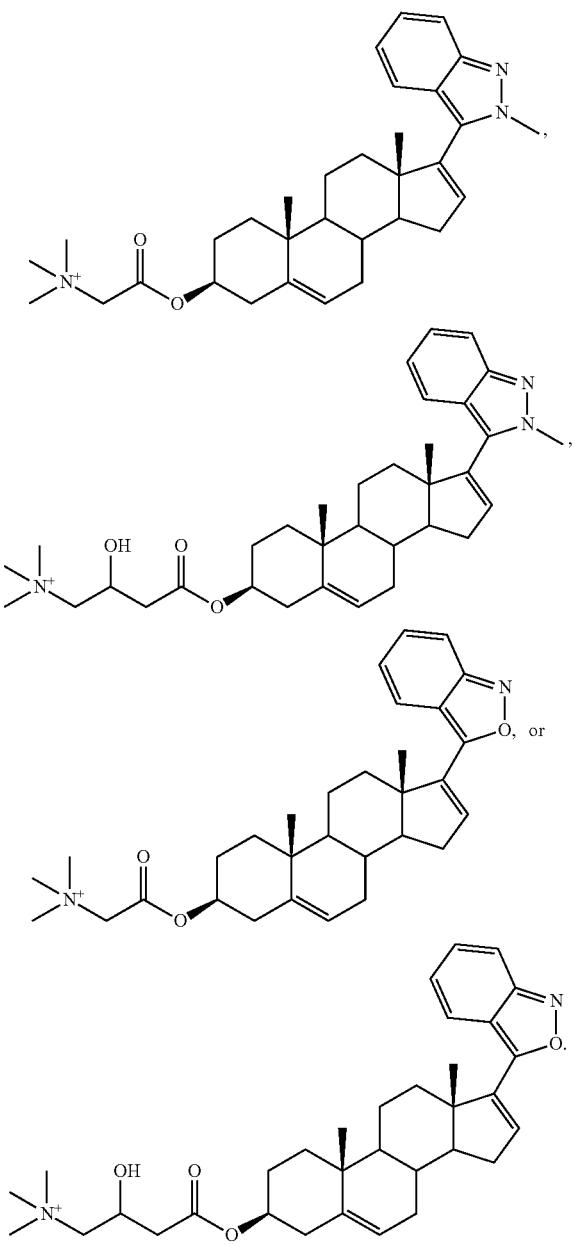

In some embodiments, the compound is represented by Formula II:

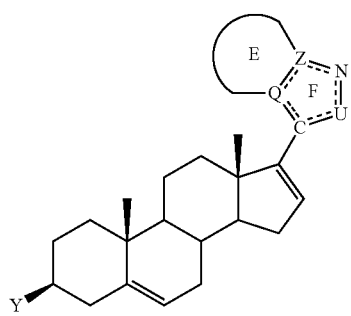

Formula II wherein:

E is a ring containing 5, 6, or 7 atoms, which together with the F-ring forms an EF group comprising a 10-electron aromatic system;

U, Z, and Q are each independently C, CH, N, NH, oxygen, or sulfur; and

Y is OH, 0-acetyl, or a physiological precursor of a 3-hydroxyl group.

In some embodiments, the EF group is 1-azaazulene, 2-alkylindazole, pyrazolo-[1,5-a]-pyridine, imidazo-[1,2-a]-pyridine, pyrrolo-[2,3-a]-pyrimidine, pyrrolo-[2,3-c]-pyrimidine, imidazo-[1,2-c]-pyrimidine, imidazo-[1,2-a]-pyrimidines4-alkylpyrazolo-[1,5-a]imidazole, 2,1-benzoxazoles, 2,1-benzthiazole, imidazo[2,1-b][1,3]oxazole, imidazo[2,1-b][1,3]thiazole, imidazo-[2,1-b][1,2]isoxazole, or cyclopenta[b]pyrrole, any of which is optionally substituted with halogen, amino, aminoalkylene, hydroxy, —SH, —S-alkyl, alkyl and halogenated $C_1$-$C_6$-alkyl.

In some embodiments, the invention provides a pharmaceutical composition comprising a therapeutically-effective amount of one or more compounds and one or more pharmaceutically-acceptable excipients, bulking agents, binders, flow agents, release agents, carriers or diluents.

In some embodiments, the composition is an oral dosage form.

In some embodiments, the oral dosage form is a tablet, a caplet, or a capsule.

In some embodiments, the amount of the compound is less than about 2000 mg.

In some embodiments, the amount of the compound is from about 500 mg to about 1500 mg.

In some embodiments, the compound is:

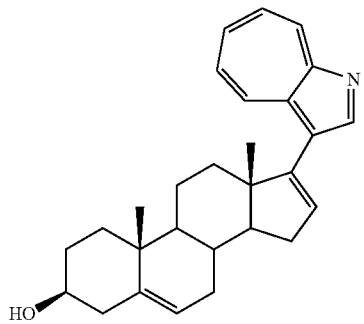

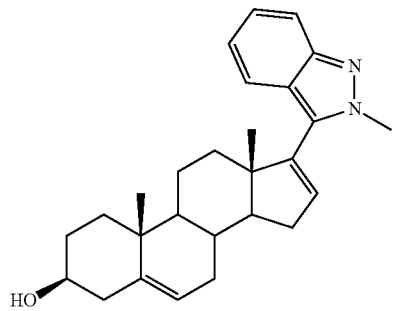

25
-continued
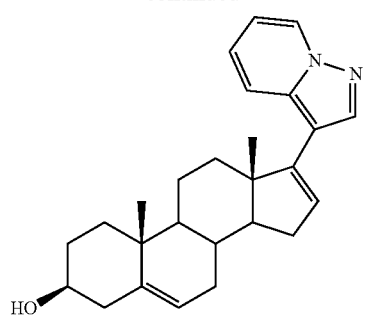
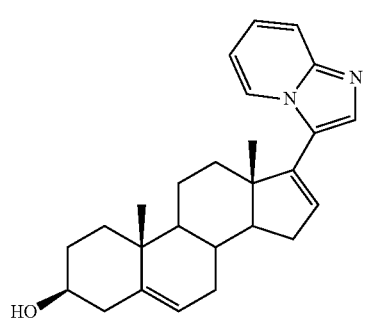
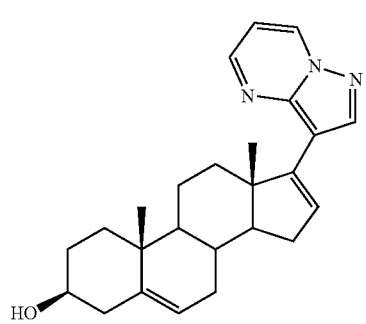
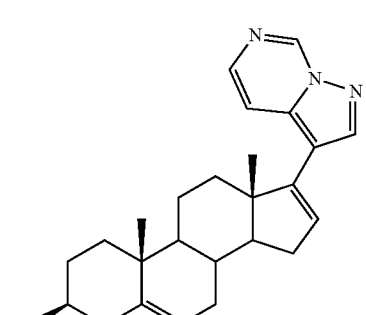
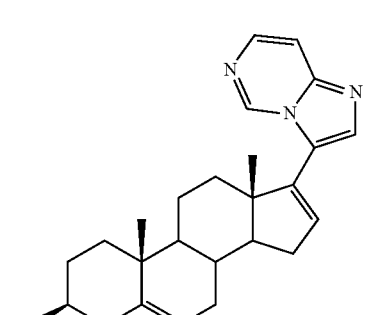
26
-continued
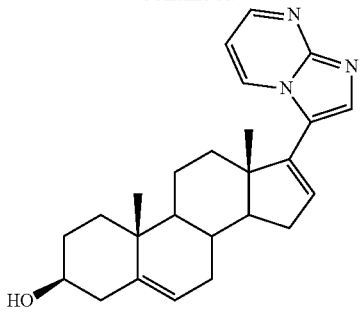
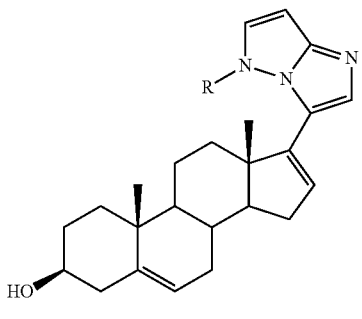
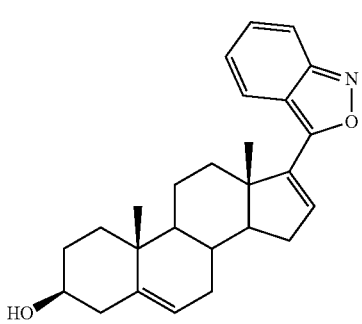
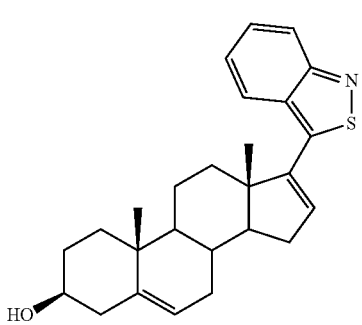
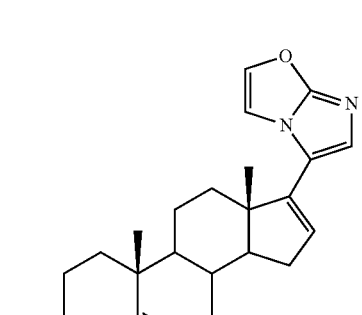

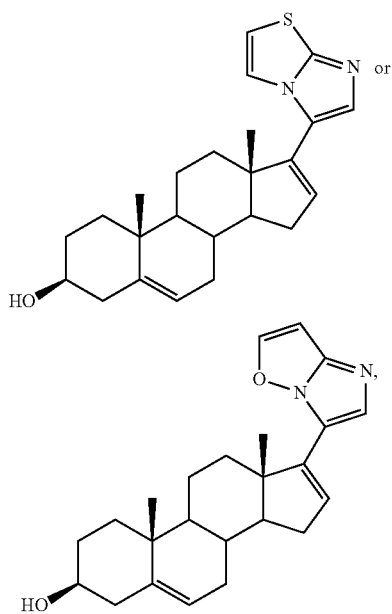

wherein R is $C_1$-$C_6$-alkyl, alkoxyalkyl, alkylaryl, aryl or heteroaryl.

In some embodiments, the compound is:

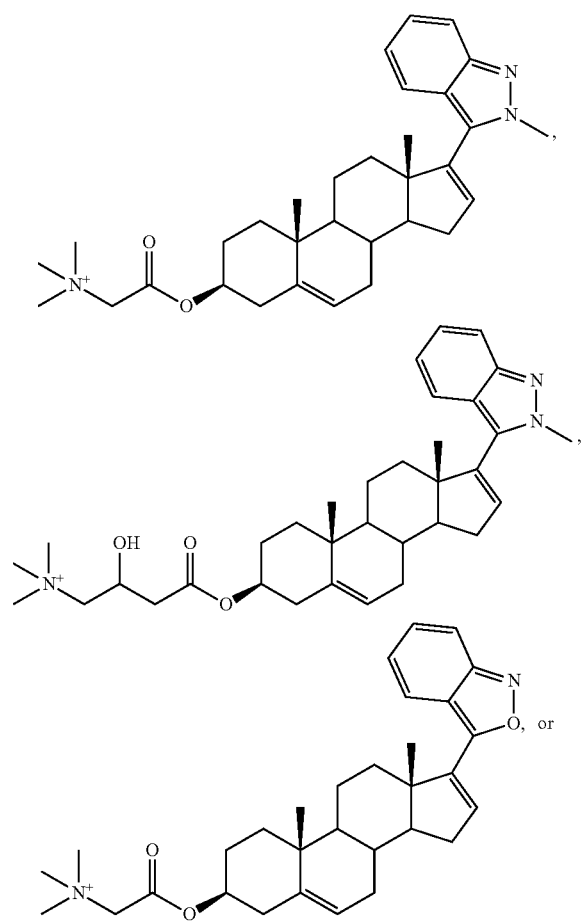

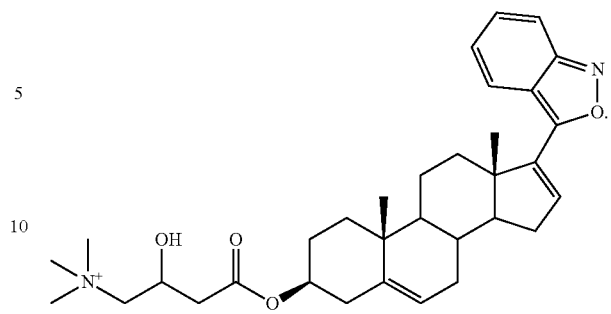

In some embodiments, the invention provides a method of treating a cancer in a subject in need or want thereof, the method comprising administering to the subject a therapeutically-effective amount of a compound.

In some embodiments, the cancer is a urogenital and/or androgen-related cancer.

In some embodiments, the urogenital and/or androgen-related cancer is prostate cancer, breast cancer, ovarian cancer, other urogenital cancer, or prostate hyperplasia.

In some embodiments, the method further comprises administering to the subject a therapeutically-effective amount of one or more of an anti-androgen, a CYP17 inhibitor, a luteinizing hormone-releasing hormone agonist, a drug for preventing androgen production, an estrogen, and a chemotherapy drug.

In some embodiments, the amount is less than about 2000 mg.

In some embodiments, the amount is from about 100 to about 500 mg.

In some embodiments, the compound is:

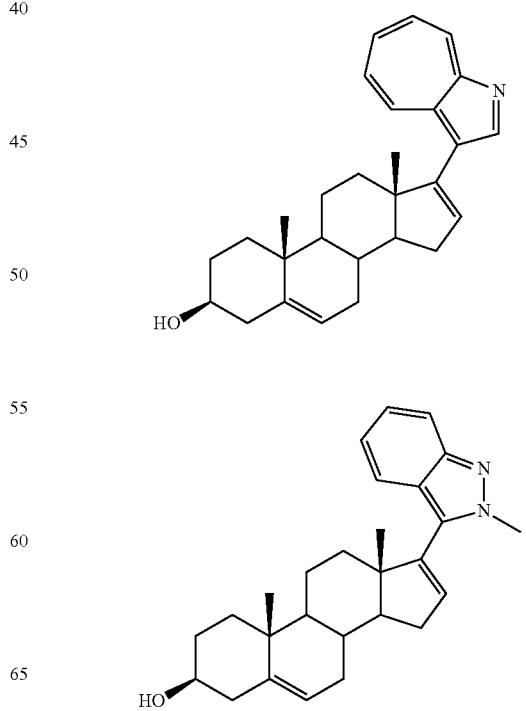

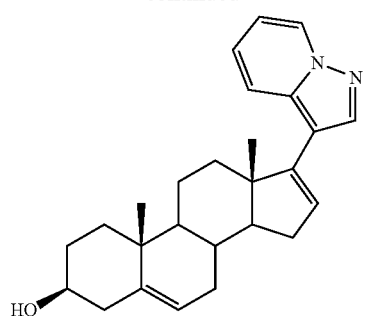
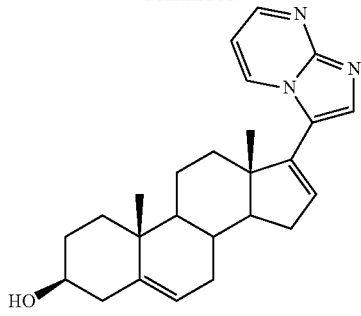
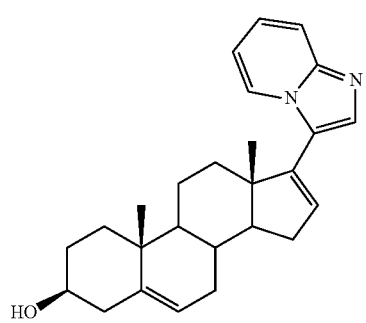
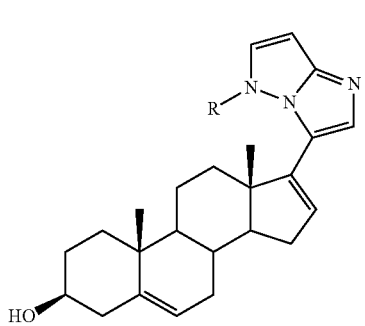
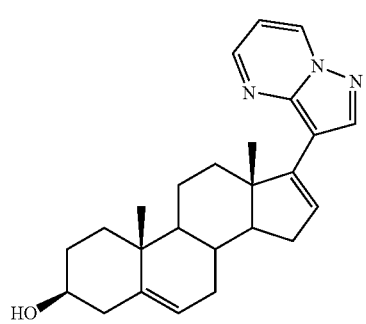
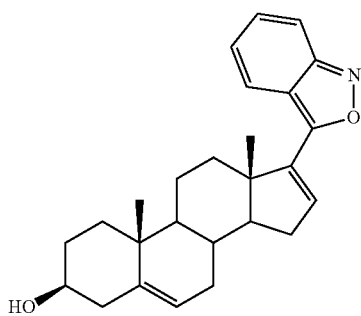
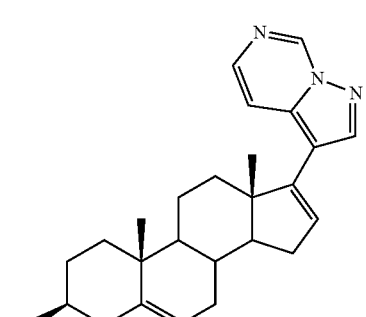
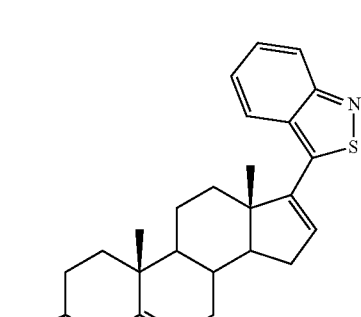
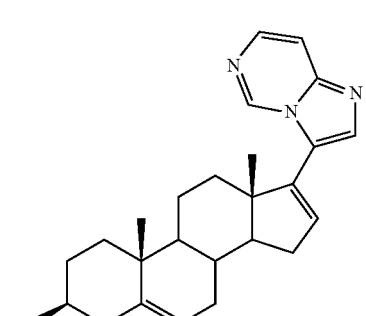
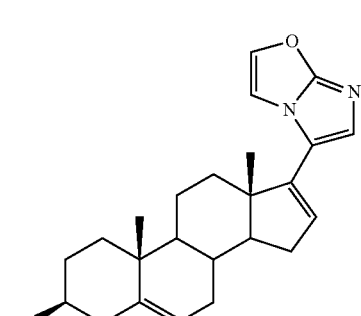

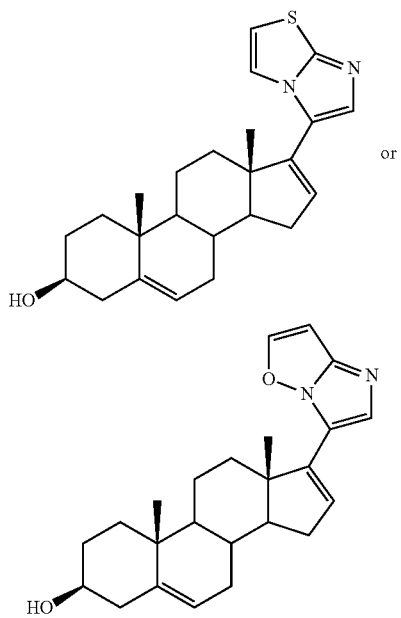

wherein R is $C_1$-$C_6$-alkyl, alkoxyalkyl, alkylaryl, aryl or heteroaryl.

In some embodiments, the compound is:

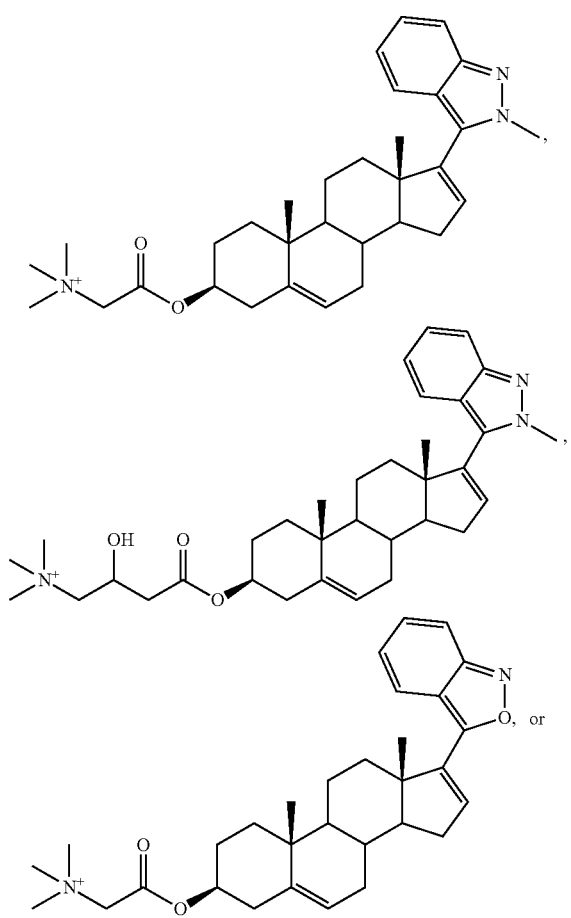

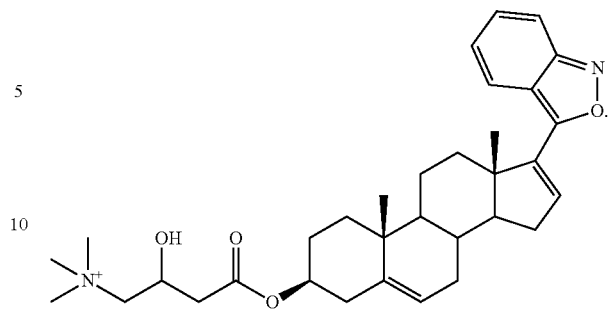

In some embodiments, the invention provides a method of treating a cancer in a subject in need or want thereof, the method comprising administering to the subject a therapeutically-effective amount of a compound of claim 1, in combination with a hormone therapy, a chemotherapy, a radiation therapy, an immunotherapy, or surgery.

In some embodiments, the cancer is a urogenital and/or androgen-related cancer.

In some embodiments, the urogenital and/or androgen-related cancer is prostate cancer, breast cancer, ovarian cancer, other urogenital cancer, or prostate hyperplasia.

In some embodiments, the amount is less than about 2000 mg.

In some embodiments, the amount is from about 100 to about 500 mg

In some embodiments, the compound is:

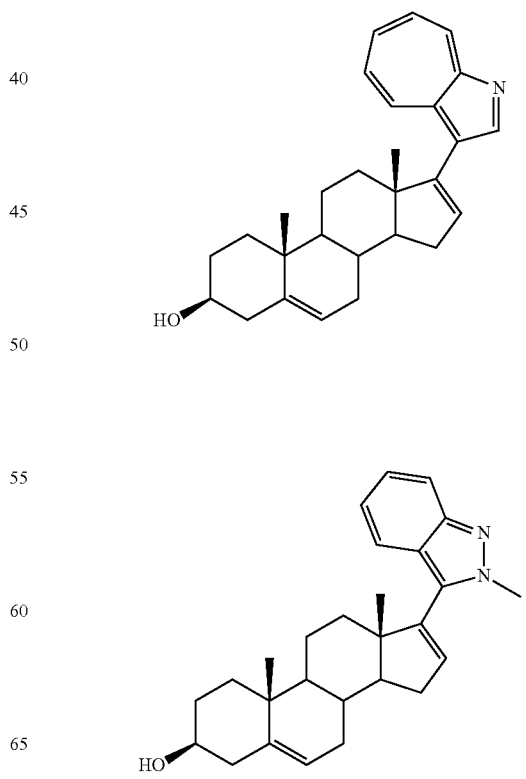

33
-continued
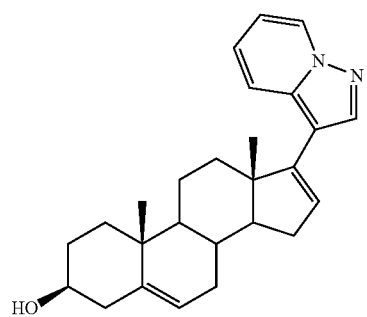
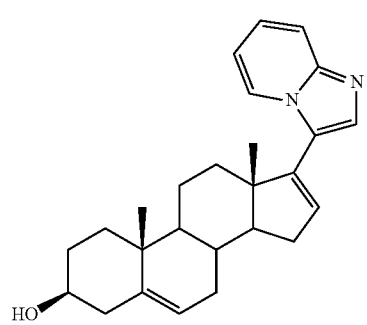
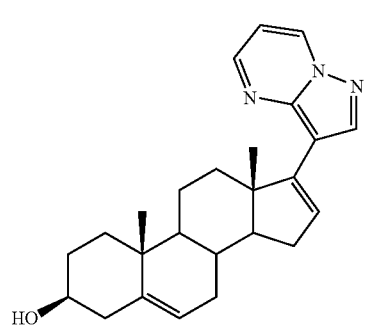
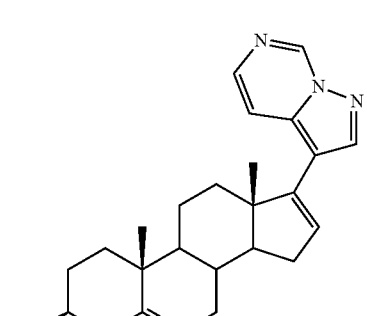
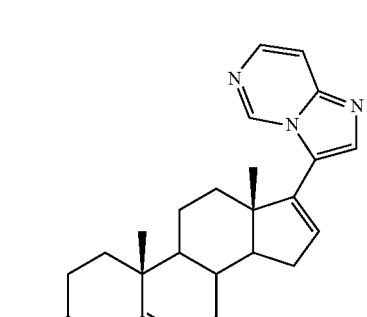
34
-continued
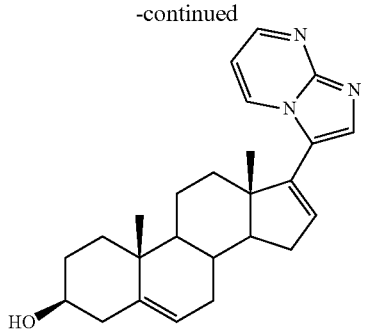
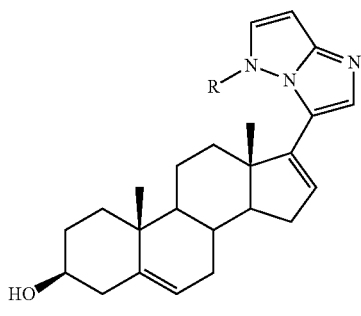
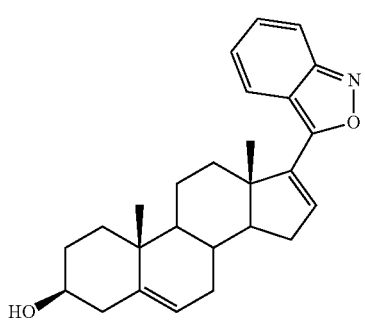
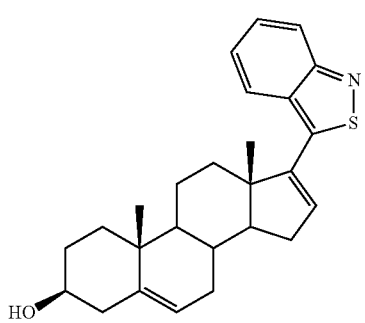
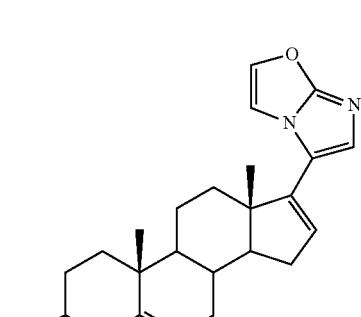

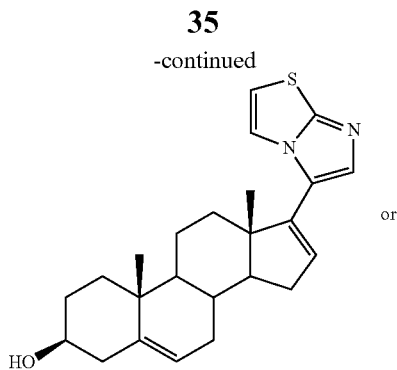

or

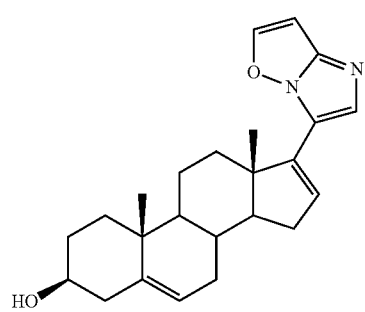

wherein R is $C_1$-$C_6$-alkyl, alkoxyalkyl, alkylaryl, aryl or heteroaryl.

In some embodiments, the compound is:

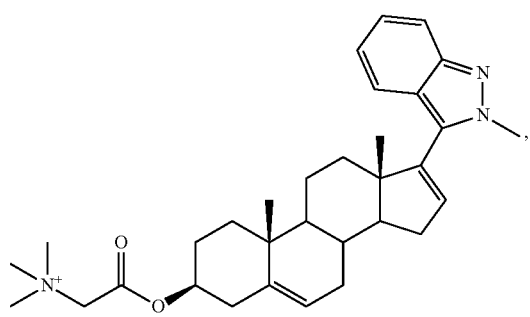

,

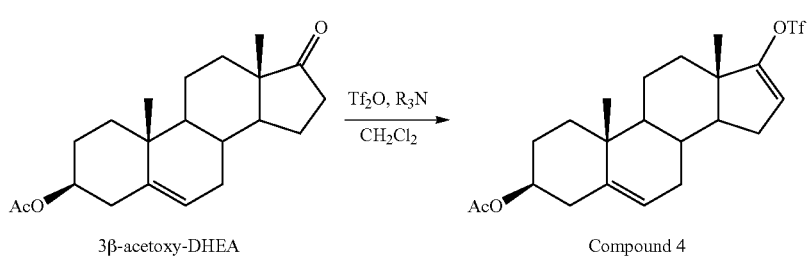

, or

Compound Preparation

The preparation of target 17-heterocyclic compounds is outlined herein as an example of synthetic strategies that are broadly applicable to the compounds of the invention.

The key intermediate in the synthesis of the 17-heteroaryl steroids, 3β-acetoxyandtrosta-5,16-dien-17-yl trifluoromethanesulfonate ester (Compound 4), was obtained by the routine procedure as previously described (Potter et al., *J. Med. Chem.*, 1995, 38, 2463-2471 and U.S. patent application Ser. No. 11/660,792). Suzuki coupling of Compound 4 with the appropriate borane, borate, boronic acid, or boronic ester affords the acetate of the desired compound. The acetate may be employed as a prodrug, or may be hydrolyzed to the alcohol:

3β-acetoxy-DHEA → Compound 4

Tf₂O, R₃N
CH₂Cl₂

1. (RO)₂BAr
   Pd(PPh₃)₂Cl₂
   NaHCO₃, THF
2. silca/celite Pad

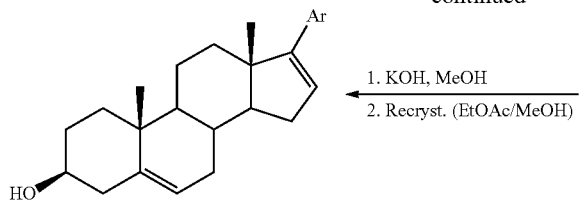
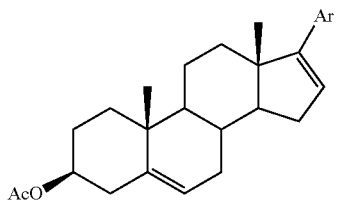

EXAMPLE 1

Synthesis of 17-(1-azaazulen-3-yl)-androsta-5,16-dien-3β-ol

An aqueous solution of $Na_2CO_3$ (20 mL, 2M) is added to a solution of 3β-acetoxyandtrosta-5,16-dien-17-yl trifluoromethanesulfonate ester (4.62 g, 10 mmol), $Pd(PPh_3)_2Cl_2$ (70 mg, 0.1 mmol) and 1-azaazulen-3-yl pinacolborane (1.33 g, 5 mmol) in THF (50 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (saturated aqueous NaCl, $Na_2SO_4$), and filtered through celite. The filtrate is concentrated in vacuo, and the residue is purified by column chromatography (silica gel, EtOAc-hexanes gradient), to afford 3β-acetoxy-17-(1-azaazulen-3-yl)-androsta-5,16-diene.

A solution of the above-prepared compound (2.20 g, 5 mmol) in methanol (20 mL) is stirred while an aqueous solution of NaOH (2M, 5 mL) is added. The mixture is heated at reflux for 15 min, cooled to ambient temperature, then poured into water (100 mL). The pH of the solution is adjusted to 7.5 by the addition of HCl (5N), and the resultant mixture is extracted with dichloromethane (3×100 mL). The combined organics are washed (5% aq. $NaHCO_3$), dried (saturated aqueous NaCl, $Na_2SO_4$), filtered and concentrated in vacuo. The residue is purified by column chromatography to afford the desired 17-(1-azaazulen-3-yl)-androsta-5,16-dien-3β-ol.

EXAMPLE 2

Synthesis of 17-(2-methylindazol-3-yl)-androsta-5,16-dien-3β-ol

An aqueous solution of $Na_2CO_3$ (20 mL, 2M) is added to a solution of 3β-acetoxyandtrosta-5,16-dien-17-yl trifluoromethanesulfonate ester (4.62 g, 10 mmol), $Pd(PPh_3)_2Cl_2$ (70 mg, 0.1 mmol) and 2-methylindazol-3-yl boronic acid (880 mg, 5 mmol) in THF (45 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (sat'd. aq. NaCl, $Na_2SO_4$), and filtered through a thick pad of silica. The filtrate is concentrated in vacuo, and the residue is purified by column chromatography (silica gel, EtOAc-hexanes gradient), to afford 3β-acetoxy-17-(2-methylindazol-3-yl)-androsta-5,16-diene.

A solution of the above-prepared compound (2.22 g, 5 mmol) in methanol (20 mL) is stirred while an aqueous solution of NaOH (2M, 5 mL) is added. The mixture is heated at reflux for 15 min, cooled to ambient temperature, then poured into water (100 mL). The pH of the solution is adjusted to 7.5 by the addition of HCl (5N), and the resultant mixture is extracted with dichloromethane (3×100 mL). The combined organics are washed (5% aq. $NaHCO_3$), dried (sat'd. aq. NaCl, $Na_2SO_4$), filtered and concentrated in vacuo. The residue is purified by column chromatography to afford the desired 17-(2-methylindazol-3-yl)-androsta-5,16-dien-3β-ol.

EXAMPLE 3

Synthesis of 17-(pyrazolo-[1,5-a]pyridin-3-yl)-androsta-5,16-dien-3β-ol

An aqueous solution of $Na_2CO_3$ (20 mL, 2M) is added to a solution of 3β-acetoxyandtrosta-5,16-dien-17-yl trifluoromethanesulfonate ester (4.62 g, 10 mmol), $Pd(PPh_3)_2Cl_2$ (70 mg, 0.1 mmol) and pyrazolo-[1,5-a]-pyridin-3-yl boronic acid (810 mg, 5 mmol) in THF (25 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (sat'd. aq. NaCl, $Na_2SO_4$), and filtered through a thick pad of silica. The filtrate is concentrated in vacuo, and the residue is purified by column chromatography (silica gel, EtOAc-hexanes gradient), to afford 3β-acetoxy-17-(pyrazolo-[1,5-a]-pyridin-3-yl)-androsta-5,16-diene.

A solution of the above-prepared compound (1.29 g, 3 mmol) in methanol (12 mL) is stirred while an aqueous solution of NaOH (2M, 3 mL) is added. The mixture is heated at reflux for 15 min, cooled to ambient temperature, then poured into water (80 mL). The pH of the solution is adjusted to 7.5 by the addition of HCl (5N), and the resultant mixture is extracted with dichloromethane (3×80 mL). The combined organics are washed (5% aq. $NaHCO_3$), dried (sat'd. aq. NaCl, $Na_2SO_4$), filtered and concentrated in vacuo. The residue is purified by column chromatography to afford the desired 17-(pyrazolo-[1,5-a]-pyridin-3-yl)-androsta-5,16-dien-3β-ol.

EXAMPLE 4

Synthesis of 17-(imidazo-[1,2-a]pyridin-3-yl)-androsta-5,16-dien-3β-ol

An aqueous solution of $Na_2CO_3$ (20 mL, 2M) is added to a solution of 3β-acetoxyandtrosta-5,16-dien-17-yl trifluoromethanesulfonate ester (4.62 g, 10 mmol), $Pd(PPh_3)_2Cl_2$ (70 mg, 0.1 mmol) and imidazo-[1,2-a]-pyridin-3-yl boronic acid (810 mg, 5 mmol) in THF (30 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (sat'd. aq. NaCl, $Na_2SO_4$), and filtered through a thick pad of silica. The filtrate is concentrated in vacuo, and the residue is purified by column chromatography (silica gel, EtOAc-hexanes gradient), to afford 3β-acetoxy-17-(imidazo-[1,2-a]-pyridin-3-yl)-androsta-5,16-diene.

A solution of the above-prepared compound (1.29 g, 3 mmol) in methanol (12 mL) is stirred while an aqueous solution of NaOH (2M, 3 mL) is added. The mixture is heated at reflux for 15 min, cooled to ambient temperature, then poured into water (80 mL). The pH of the solution is adjusted to 7.5 by the addition of HCl (5N), and the resultant mixture is extracted with dichloromethane (3×80 mL). The combined organics are washed (5% aq. NaHCO₃), dried (sat'd. aq. NaCl, Na₂SO₄), filtered and concentrated in vacuo. The residue is purified by column chromatography to afford the desired 17-(imidazo-[1,2-a]-pyridin-3-yl)-androsta-5,16-dien-3β-ol.

EXAMPLE 5

Synthesis of 17-(imidazo-[1,2-a]pyrimidin-3-yl)-androsta-5,16-dien-3β-ol

An aqueous solution of Na₂CO₃ (4 mL, 2M) is added to a solution of 3β-acetoxyandtrosta-5,16-dien-17-yl trifluoromethanesulfonate ester (924 mg, 2 mmol), Pd(PPh₃)₂Cl₂ (14 mg, 0.02 mmol) and imidazo-[1,2-a]-pyrimidin-3-yl boronic acid (163 mg, 1 mmol) in THF (5 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (sat'd. aq. NaCl, Na₂SO₄), and filtered through a thick pad of silica. The filtrate is concentrated in vacuo, and the residue is purified by column chromatography (silica gel, EtOAc-hexanes gradient), to afford 3β-acetoxy-17-(imidazo-[1,2-a]-pyrimidin-3-yl)-androsta-5,16-diene.

A solution of the above-prepared compound (215 mg, 0.5 mmol) in methanol (2 mL) is stirred while an aqueous solution of NaOH (2M, 0.5 mL) is added. The mixture is heated at reflux for 15 min, cooled to ambient temperature, then poured into water (15 mL). The pH of the solution is adjusted to 7.5 by the addition of HCl (5N), and the resultant mixture is extracted with dichloromethane (3×20 mL). The combined organics are washed (5% aq. NaHCO₃), dried (sat'd. aq. NaCl, Na₂SO₄), filtered and concentrated in vacuo. The residue is purified by column chromatography to afford the desired 17-(imidazo-[1,2-a]-pyrimidin-3-yl)-androsta-5,16-dien-3β-ol.

EXAMPLE 6

Synthesis of 17-(2,1-benzoxazol-3-yl)-androsta-5,16-dien-3β-ol

An aqueous solution of Na₂CO₃ (4 mL, 2M) is added to a solution of 3β-acetoxyandtrosta-5,16-dien-17-yltrifluoromethanesulfonate ester (924 mg, 2 mmol), Pd(PPh₃)₂Cl₂ (14 mg, 0.02 mmol) and 2,1-benzoxazol-3-yl pinacolborane (245 mg, 1 mmol) in THF (5 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (sat'd. aq. NaCl, Na₂SO₄), and filtered through a pad of silica/celite. The filtrate is concentrated in vacuo, and the residue is purified by column chromatography (silica gel, EtOAc-hexanes gradient), to afford 3β-acetoxy-17-(2,1-benzoxazol-3-yl)-androsta-5,16-diene.

A solution of the above-prepared compound (129 mg, 0.3 mmol) in methanol (2 mL) is stirred while an aqueous solution of NaOH (2M, 300 μL) is added. The mixture is heated at 80° C. for 15 min, cooled to ambient temperature, then poured into water (10 mL). The pH of the solution is adjusted to 7.5 by the addition of HCl (5N), and the resultant mixture is extracted with dichloromethane (3×15 mL). The combined organics are washed (5% aq. NaHCO₃), dried (sat'd. aq. NaCl, Na₂SO₄), filtered and concentrated in vacuo. The residue is purified by column chromatography to afford the desired 17-(2,1-benzoxazol-3-yl)-androsta-5,16-dien-3β-ol.

EXAMPLE 7

Synthesis of 17-(imidazo[2,1-b][1,3]oxazol-5-yl)-androsta-5,16-dien-3β-ol

An aqueous solution of Na₂CO₃ (15 mL, 2M) is added to a solution of 3β-acetoxyandtrosta-5,16-dien-17-yltrifluoromethanesulfonate ester (3.70 g, 8 mmol), Pd(PPh₃)₂Cl₂ (57 mg, 0.08 mmol) and imidazo[2,1-b][1,3]oxazol-5-yl pinacolborane (936 mg, 4 mmol) in THF (40 mL), and the resultant mixture is heated at 80° C. for 1 hour. The mixture is cooled and poured into water (100 mL) and ether (100 mL). The aqueous phase is separated and extracted with ether (2×100 mL) and the combined organics are dried (sat'd. aq. NaCl, Na₂SO₄), and filtered through a thick pad of silica. The filtrate is concentrated in vacuo, and the residue is purified by column chromatography (silica gel, EtOAc-hexanes gradient), to afford 3β-acetoxy-17-(imidazo[2,1-b][1,3]oxazol-5-yl)-androsta-5,16-diene.

A solution of the above-prepared compound (839 mg, 2 mmol) in methanol (5 mL) is stirred while an aqueous solution of NaOH (2M, 2 mL) is added. The mixture is heated at reflux for 15 min, cooled to ambient temperature, then poured into water (100 mL). The pH of the solution is adjusted to 7.5 by the addition of HCl (5N), and the resultant mixture is extracted with dichloromethane (3×100 mL). The combined organics are washed (5% aq. NaHCO₃), dried (sat'd. aq. NaCl, Na₂SO₄), filtered and concentrated in vacuo. The residue is purified by column chromatography to afford the desired 17-(imidazo[2,1-b][1,3]oxazol-5-yl)-androsta-5,16-dien-3β-ol.

What is claimed is:

1. A compound of Formula I:

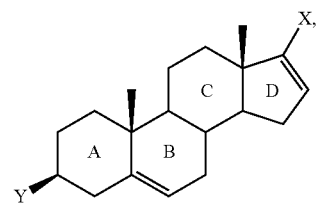

Formula I wherein:

each position of the ABC ring structure is independently optionally substituted;

X is any one of

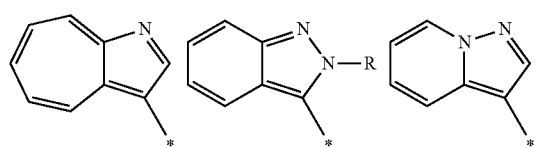

-continued

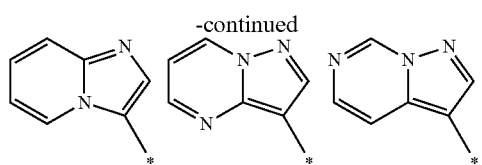

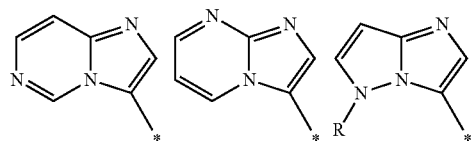

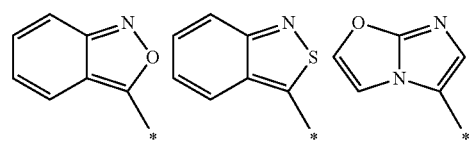

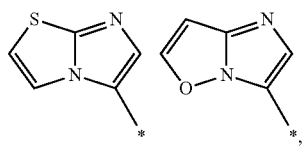

wherein * is the point of attachment, and R is $C_1$-$C_6$-alkyl, alkoxyalkyl, alkylaryl, aryl or heteroaryl, and wherein any of the foregoing groups are optionally substituted; and Y is OH, an ester, or a pharmaceutically-acceptable salt thereof.

2. The compound of claim 1, wherein each position of the ABC ring structure is independently optionally substituted with one or more of alkyl, halogenated alkyl, alkenyl, halogenated alkenyl, halogen, amino, aminoalkylene, hydroxyimino, and hydroxy.

3. The compound of claim 2, wherein X is optionally substituted with one or more of halogen, amino, aminoalkylene, hydroxy, —SH, —S-alkyl, alkyl and halogenated $C_1$-$C_6$-alkyl.

4. The compound of claim 3, wherein Y is OH.

5. The compound of claim 4, wherein the compound is any one of:

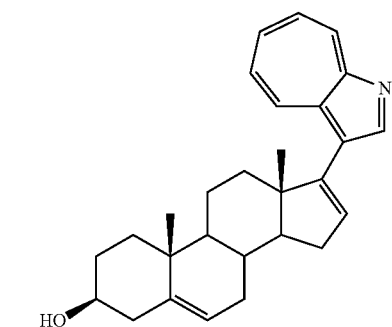

-continued

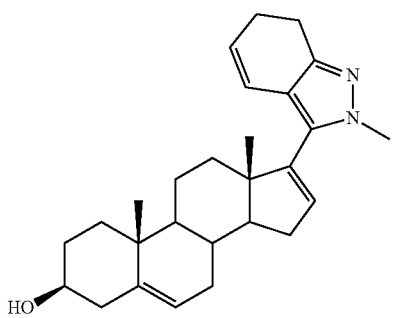

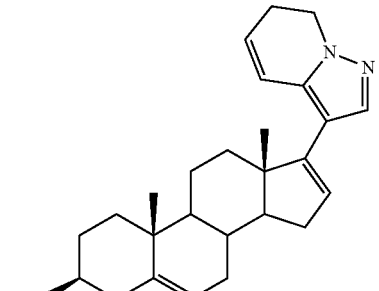

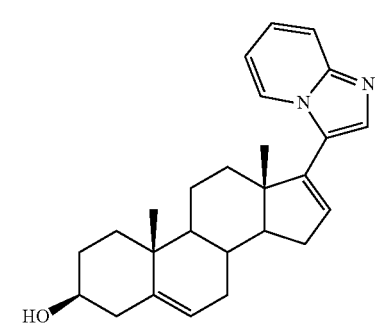

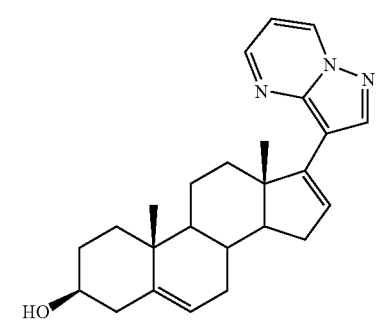

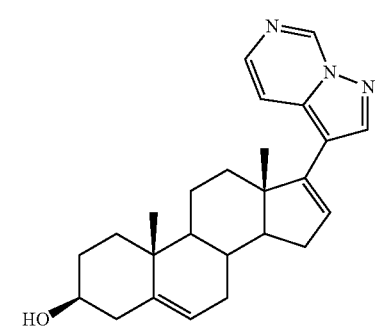

43
-continued
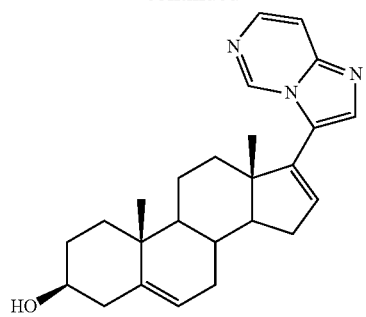
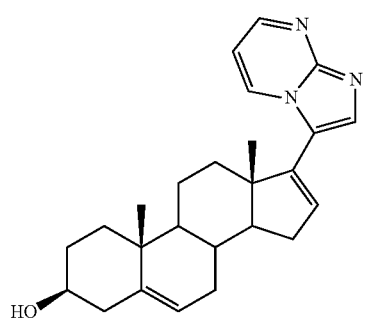
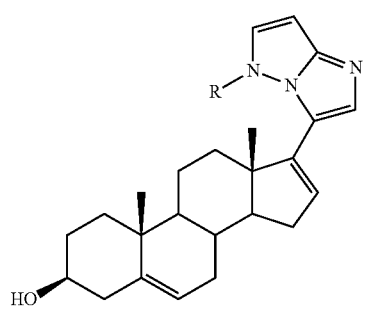
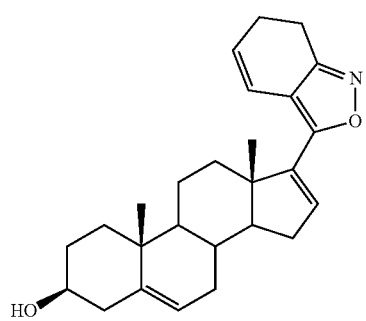
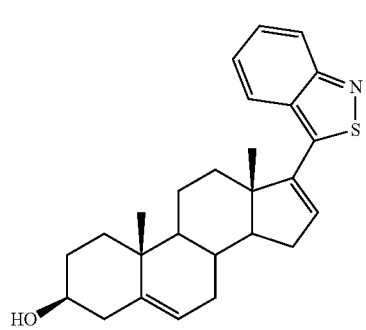
44
-continued
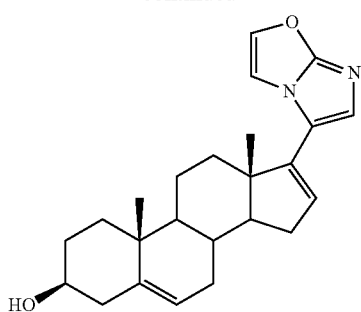
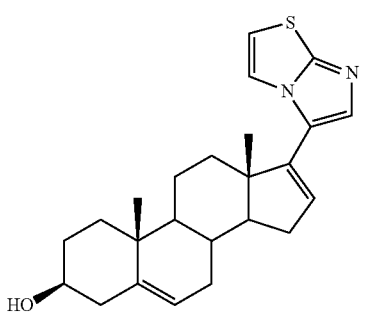
or
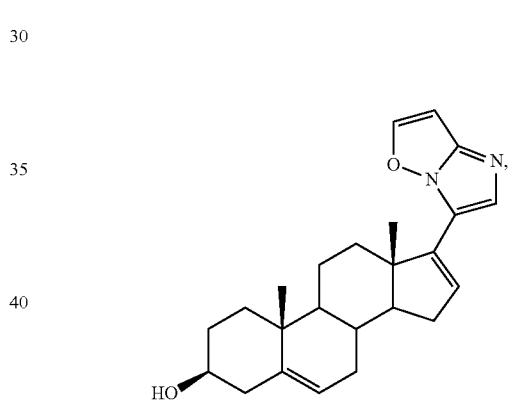
wherein R is $C_1$-$C_6$-alkyl, alkoxyalkyl, alkylaryl, aryl or heteroaryl.
6. The compound of claim 3, wherein Y is O-acetyl, O-propionyl, O-betaine O-carnitine an amino acid group, or a peptidyl group.
7. The compound of claim 6, wherein the compound is:
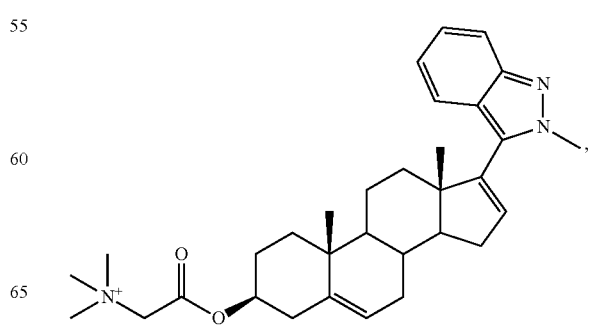

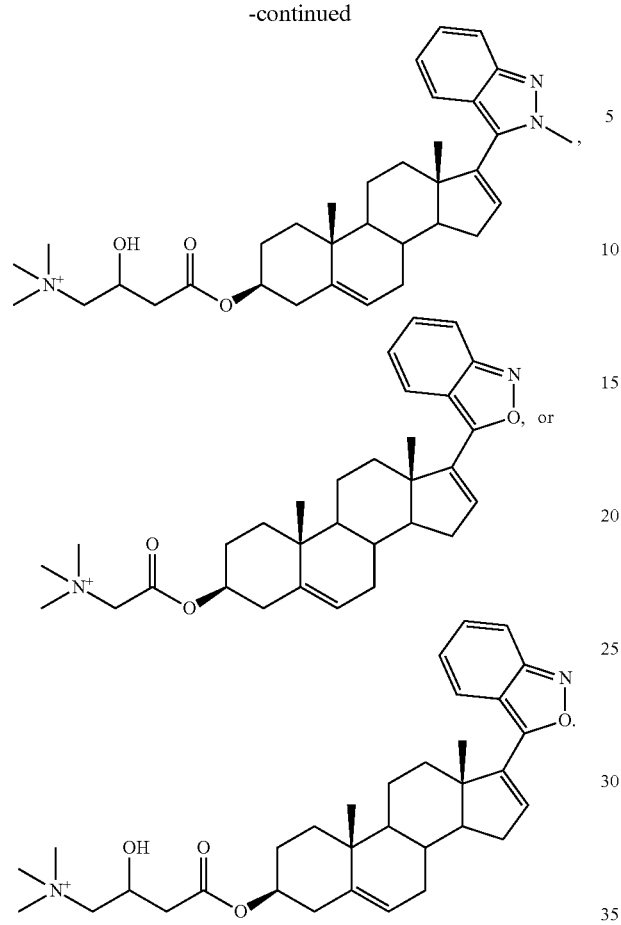

8. A pharmaceutical composition comprising a therapeutically-effective amount of one or more compounds of claim 1 and one or more pharmaceutically-acceptable excipients, bulking agents, binders, flow agents, release agents, carriers or diluents.

9. The pharmaceutical composition of claim 8, wherein the composition is an oral dosage form.

10. The pharmaceutical composition of claim 9, wherein the oral dosage form is a tablet, a caplet, or a capsule.

11. The pharmaceutical composition of claim 8, wherein the amount of the compound is less than 2000 mg.

12. The pharmaceutical composition of claim 8, wherein the amount of the compound is from about 500 mg to about 1500 mg.

13. The pharmaceutical composition of claim 8, wherein the compound is:

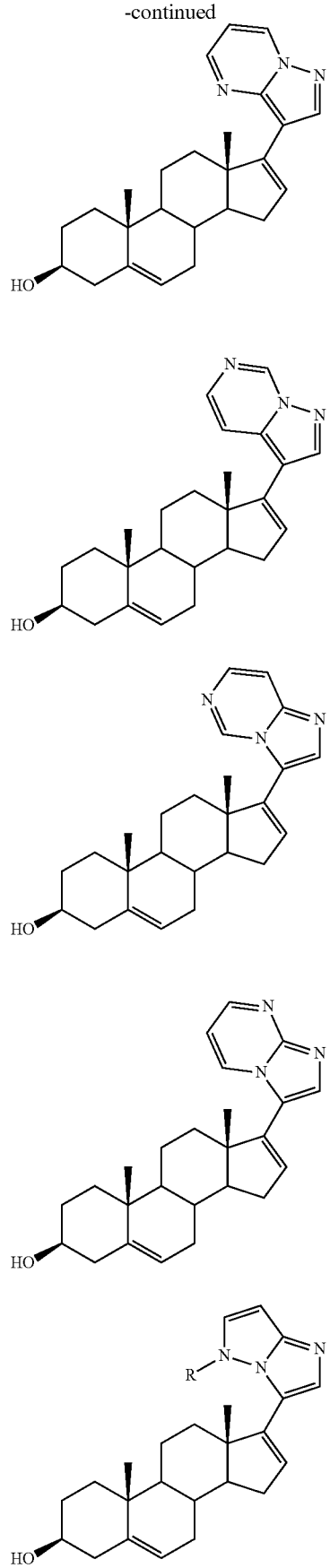

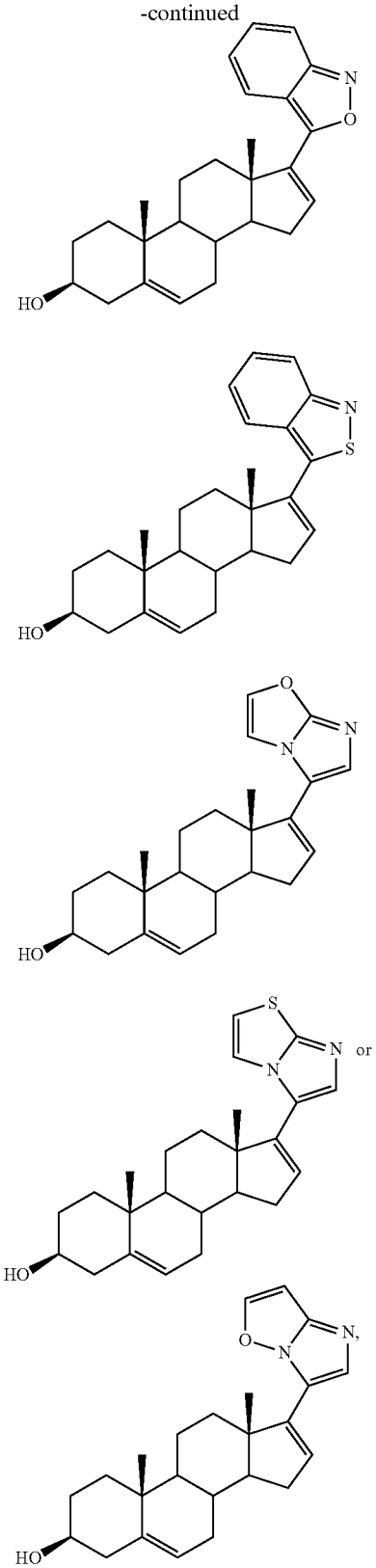

wherein R is $C_1$-$C_6$-alkyl, alkoxyalkyl, alkylaryl, aryl or heteroaryl.

14. The pharmaceutical composition of claim 8, wherein the compound is:

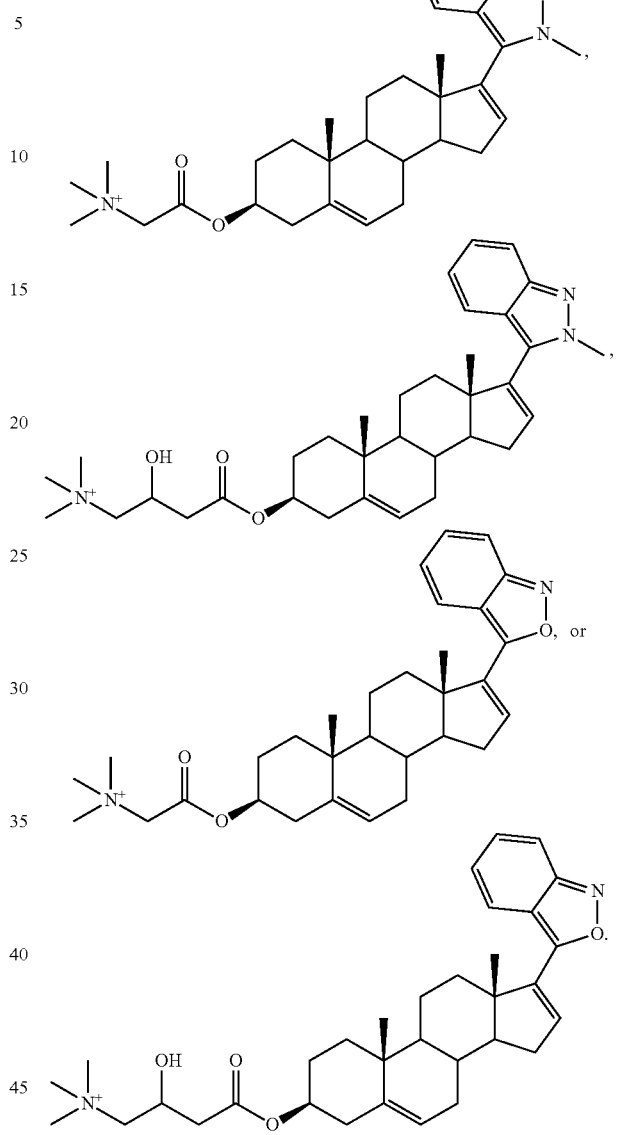

15. A method of treating a prostate cancer in a subject in need thereof, the method comprising administering to the subject a therapeutically-effective amount of a compound of claim 1.

16. The method of claim 15, further comprising administering to the subject a therapeutically-effective amount of one or more of an anti-androgen, a CYP17 inhibitor, a luteinizing hormone-releasing hormone agonist, a 5α-reductase inhibitor, an estrogen, and a chemotherapy drug.

17. The method of claim 16, wherein the anti-androgen is flutamide, nilutamide, ketoconazole, aminoglutethimide, or abiraterone.

18. The method of claim 16, wherein the luteinizing hormone-releasing hormone agonist is leuprolide, goserelin or buserelin.

19. The method of claim 15, wherein the amount is less than 2000 mg.

20. The method of claim 15, wherein the amount is from about 100 to about 500 mg.

21. The method of claim 15, wherein the compound is:
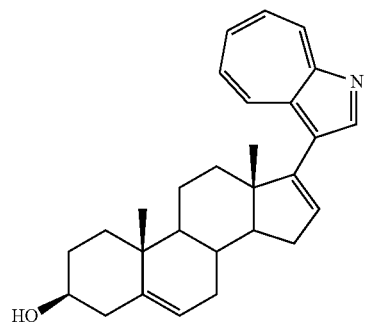
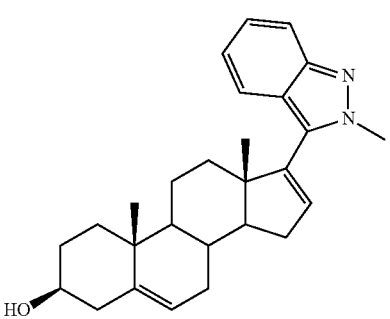
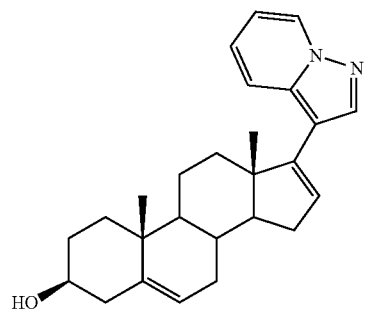
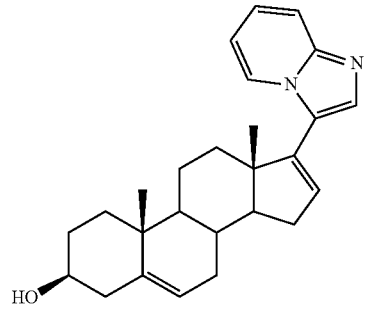
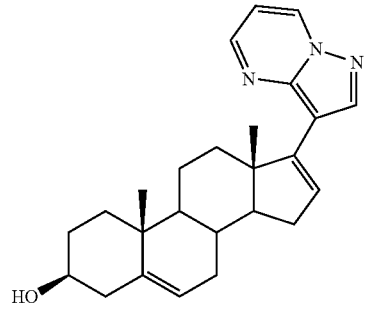
-continued
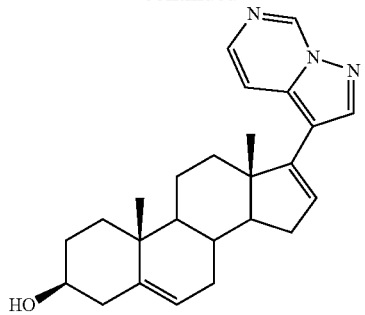
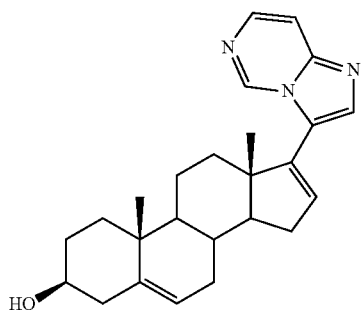
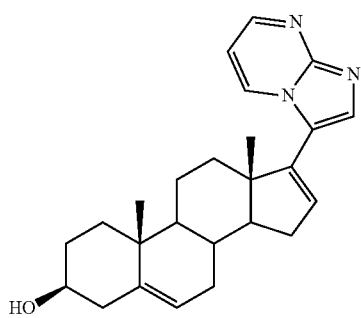
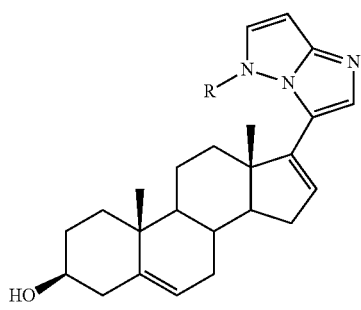
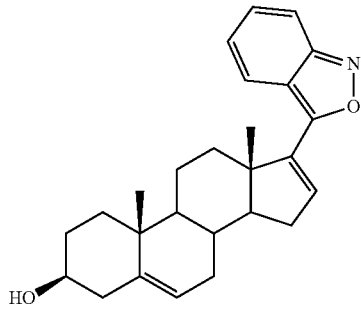

51
-continued

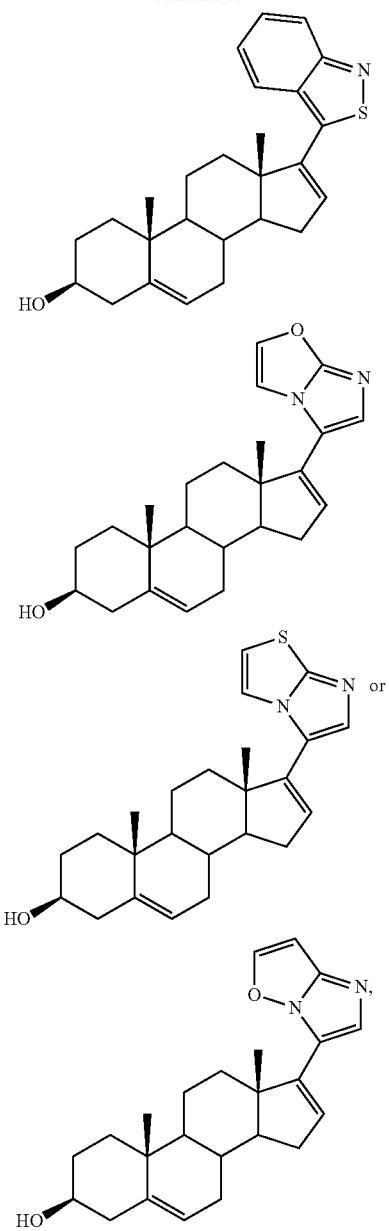

wherein R is $C_1$-$C_6$-alkyl, alkoxyalkyl, alkylaryl, aryl or heteroaryl.

22. The method of claim 15, wherein the compound is:

52
-continued

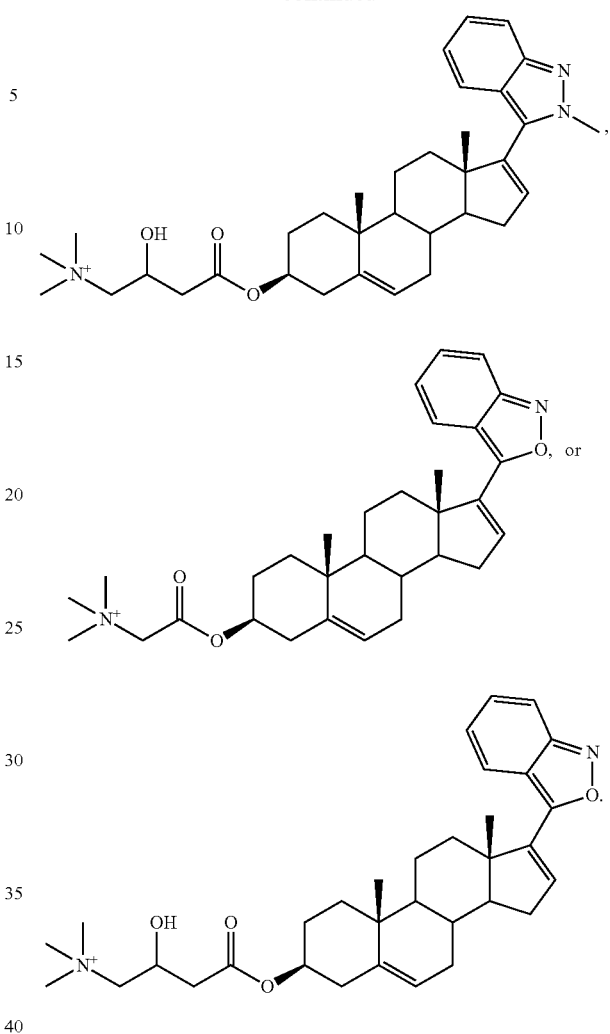

23. A method of treating a prostate cancer in a subject in need thereof, the method comprising administering to the subject a therapeutically-effective amount of a compound of claim 1, in combination with a hormone therapy, a chemotherapy, a radiation therapy, an immunotherapy, or surgery.

24. The method of claim 23, wherein the amount is less than 2000 mg.

25. The method of claim 23, wherein the amount is from about 100 to about 500 mg.

26. The method of claim 23, wherein the compound is:

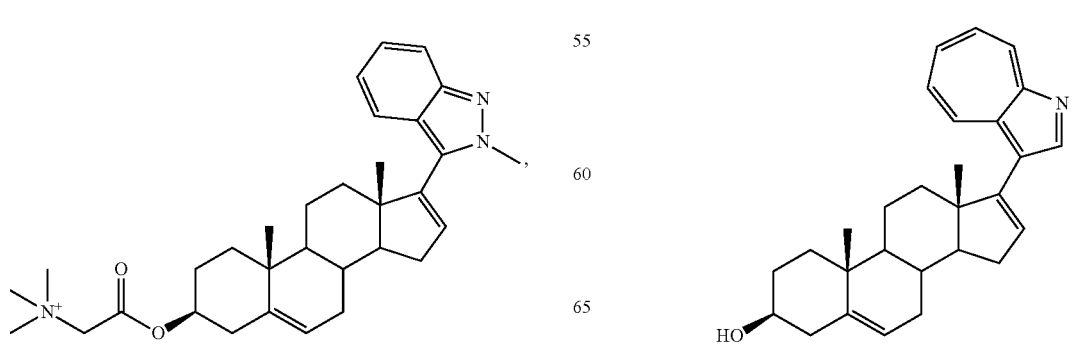

53
-continued
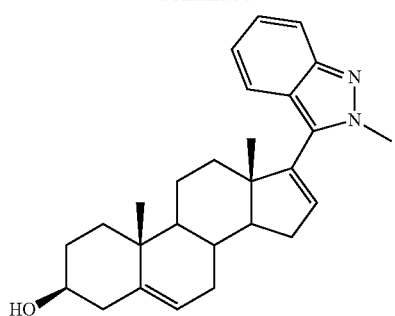
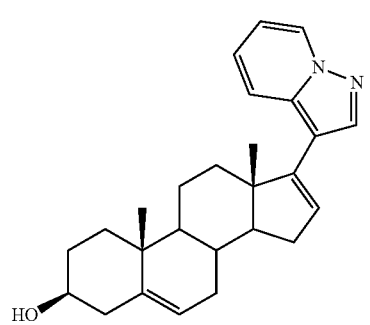
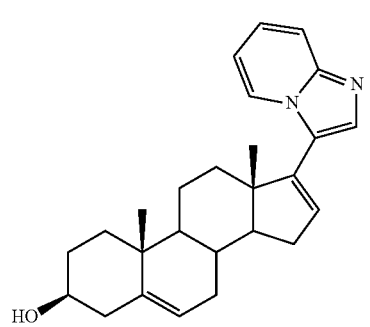
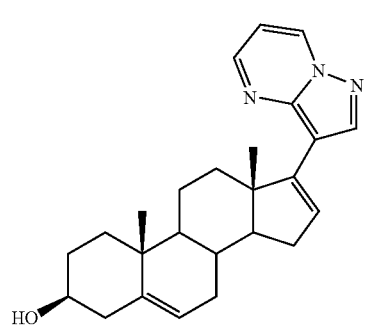
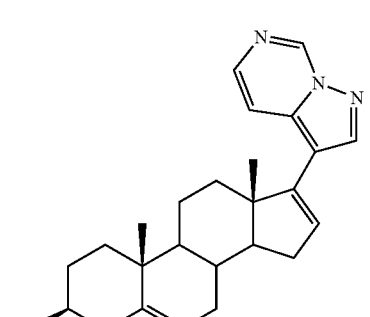
54
-continued
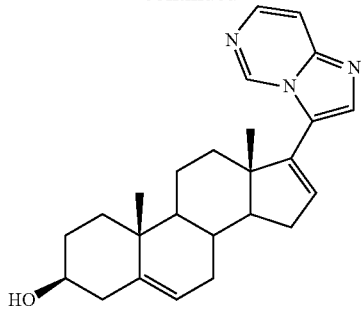
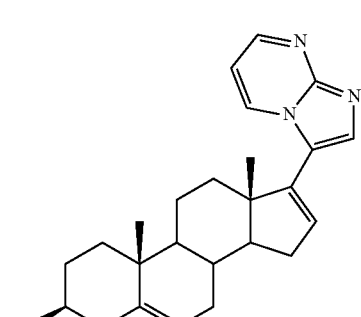
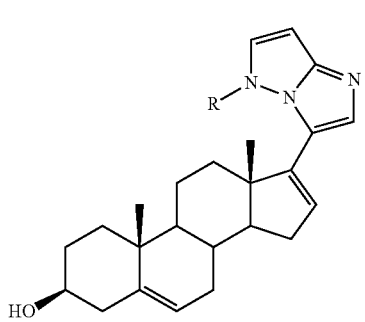
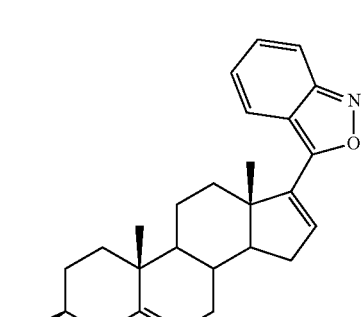
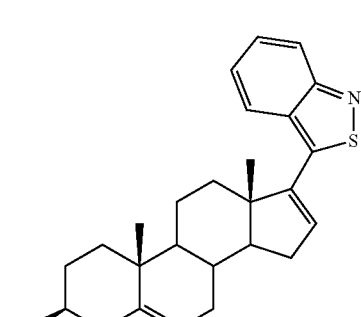

-continued
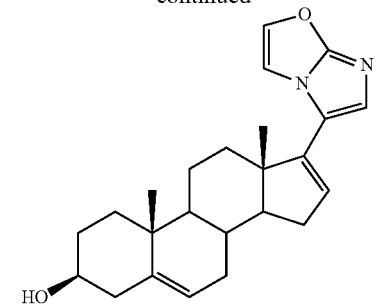
wherein R is $C_1$-$C_6$-alkyl, alkoxyalkyl, alkylaryl, aryl or heteroaryl.
27. The method of claim 23, wherein the compound is:
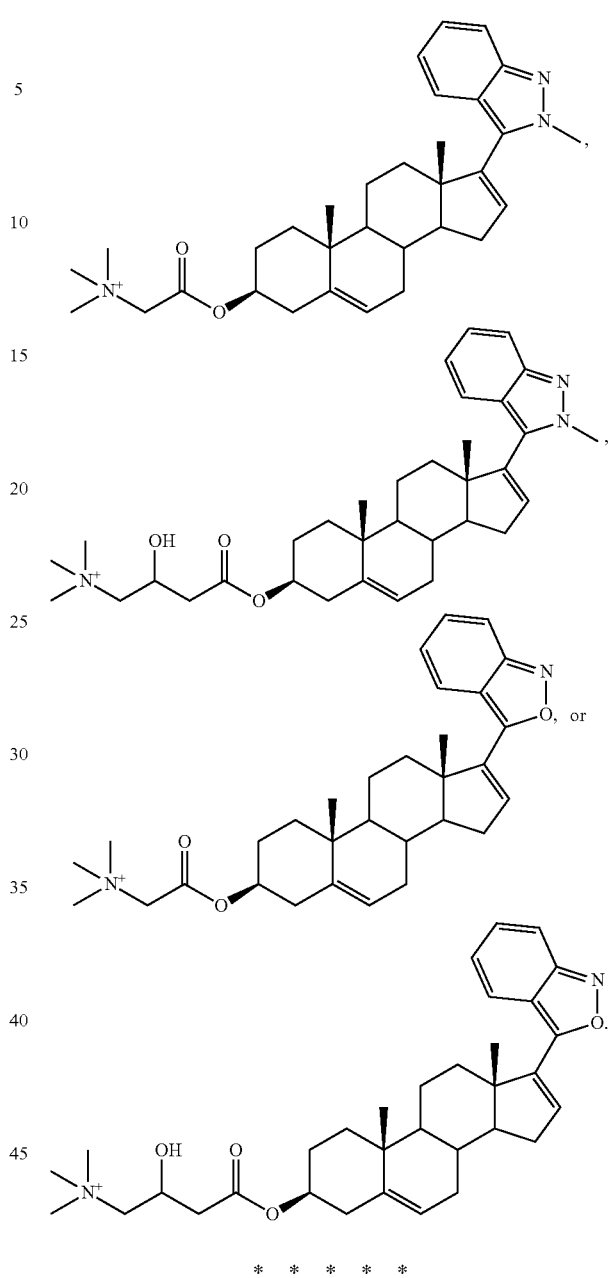
* * * * *